(12) United States Patent
Lalvani

(10) Patent No.: US 7,135,280 B2
(45) Date of Patent: Nov. 14, 2006

(54) ASSAY TO DETERMINE EFFICACY OF TREATMENT FOR MYCOBACTERIAL INFECTION

(75) Inventor: Ajit Lalvani, Oxford (GB)

(73) Assignee: Isis Innovation Limited, Oxford (GB)

( * ) Notice: Subject to any disclaimer, the term of this patent is extended or adjusted under 35 U.S.C. 154(b) by 230 days.

(21) Appl. No.: 10/451,918

(22) PCT Filed: Jan. 8, 2002

(86) PCT No.: PCT/GB02/00055

§ 371 (c)(1),
(2), (4) Date: Oct. 23, 2003

(87) PCT Pub. No.: WO02/054072

PCT Pub. Date: Jul. 11, 2002

(65) Prior Publication Data

US 2004/0058399 A1  Mar. 25, 2004

Related U.S. Application Data

(60) Provisional application No. 60/259,868, filed on Jan. 8, 2001.

(30) Foreign Application Priority Data

Jan. 8, 2001  (GB) ................................. 0100432.4

(51) Int. Cl.
*C12Q 1/00* (2006.01)
*A61K 39/04* (2006.01)

(52) U.S. Cl. ............................ 435/4; 424/9.1; 424/9.2; 424/130.1; 424/164.1; 424/184.1; 424/234.1; 424/248.1; 435/29; 435/243; 435/253.1; 436/501

(58) Field of Classification Search ................. 424/9.1, 424/9.2, 130.1, 164.1, 184.1, 234.1, 248.1; 435/4, 29, 243, 253.1; 436/501
See application file for complete search history.

(56) References Cited

FOREIGN PATENT DOCUMENTS

| WO | WO 98/23960 | 6/1998 |
| WO | WO 00/26248 | 5/2000 |
| WO | WO 00/55194 | 9/2000 |
| WO | WO 01/04151 A2 | 1/2001 |

OTHER PUBLICATIONS

Lind, A., et al, "Mycobacterial species: immunological classification", in, The Mycobacteria, a sourcebook, Part A, eds, Kubica and Wayne, Marcel Dekker, Inc., New York; pp. 67-82, 1984.*

Magnusson, M., "Immunological classification susing sensitins", in, The Mycobacteria, a sourcebook, Part A, eds, Kubica and Wayne, Marcel Dekker, Inc., New York, pp. 83-104, 1984.*

Cambau, E., et al "Resistance to quinolones in mycobaceria", Res. Microbiol., vol. 147, No. 1, pp. 52-59, 1996.*

Lalvani et al. "Human cytolytic and interferon γ-secreting $CD8^+T$ lymphocytes specific for *Mycobacterium tuberculosis*" Proc. Natl. Acad. Sci. USA 95:270-275 (1998).

Lalvani et al. "Rapid effector function in $CD8^+$memory T cells" J. Exp. Med. 186:859-865 (1997).

Pathan et al. "High frequencies of circulating IFN-γ-secreting CD8 cytotoxic T cells specific for a novel MHC class I-restricted *Mycobacterium tuberculosis* epitope in *M. tuberculosis*-infected subjects without disease" Eur. J. Immunol. 30:2713-2721 (2000).

Mustafa et al. "Comparison of antigen-specific T-cell responses of tuberculosis patients using complex or single antigens of *Mycobacterium tuberculosis*" Scand. J. Immunol. 48:535-543 (1998).

Ravn et al. "Human T cells responses to the ESAT-6 antigen from *Mycobacterium tuberculosis*" J. Infect. Dis. 179:637-645 (1999).

Search Report dated Jul. 16, 2001 for GB0100432.4.

Dieli et al. "Sequestration of T lymphocytes to body fluids in tuberculosis: Reversal of anergy following chemotherapy" XP-002214600 J. Infect. Dis. 180:225-228 (1999).

Pathan et al. "Direct ex vivo analysis of antigen-specific IFN-gamma-secreting CD4 T cells in mycobacterium tuberculosis-infected individuals: Associations with clinical disease state and effect of treatment" Abstract XP-002214601 Database Accession No. NLM11673535 J. Immunol. 167:5217-5225 (2001).

Ulrichs et al. "Differential T cell responses to mycobacterium tuberculosis ESAT6 in tuberculosis patients and healthy donors" XP-000891644 Eur. J. Immunol. 28:3949-3958 (1998).

International Search Report dated Mar. 13, 2003.

Meister et al. "Two novel T cell epitope prediction algorithms based on MHC-binding motifs; comparison of predicted and published epitopes from *Mycobacterium tuberculosis* and HIV protein sequences" Vaccine 13:581-591 (1995).

Mohagheghpour et al. "CTL response to *Mycobacterium tuberculosis*: Identification of an immunogenic epitope in the 19-kDa lipoprotein" J. Immunol. 161:2400-2406 (1998).

Smith et al. "Human CD8 CTL specific for the mycobacterial major secreted antigen 85A" J. Immunol. 165:7088-7095 (2000).

Wilkinson et al. "38 000 MW antigen-specific major histocompatibility complex class I restricted interferon-γ-secreting CD8 T cells in healthy contacts of tuberculosis" Immunol. 95:585-590 (1998).

* cited by examiner

*Primary Examiner*—Rodney P Swartz
(74) *Attorney, Agent, or Firm*—Nixon & Vanderhye

(57) ABSTRACT

Method of determining the efficacy of treatment for mycobacterial infection in an individual comprising determining in samples from the individual whether the level of T cells specific for a mycobacterial antigen has decreased after the treatment, thereby determining the efficacy of the treatment.

13 Claims, 7 Drawing Sheets

Frequencies of ESAT-6-specific IFN-gamma-secreting T cells in tuberculosis patients Frequences of IFN-gamma-secreting peptide-specific T cells specific for ESAT-6, CFP10 and PPD in 100 healthy adults in Mumbai, India Frequences of IFN-gamma-secreting peptide-specific T cells specific for ESAT-6, CFP10 and PPD in 40 healthy adults in Oxford, UK Epitope mapping of ESAT-6 in Indian TB patients (n=50)

Epitope mapping of ESAT-6 in healthy Indian adults (n=100)

Epitope mapping of CFP10 in healthy Indian adults (n=100)

Decline in frequency of ESAT-6 peptide-specific T cells during anti-tuberculosis therapy

ASSAY TO DETERMINE EFFICACY OF TREATMENT FOR MYCOBACTERIAL INFECTION

This application is a national phase application of International Patent Appln. No. PCT/GB02/00055 filed Jan. 8, 2002; which claims the benefit of provisional Appln. No. 60/259,868, filed Jan. 8, 2001.

The invention relates to a method of monitoring the progress of a mycobacterial infection and to a method of detecting latent mycobacterial infection.

In healthy individuals with latent infection, there is no means of monitoring whether the bacilli remain viable or not. The existing test for latent *M. tuberculosis* infection is the tuberculin skin test (TST), and this remains positive even after *M. tuberculosis* bacilli have been killed with appropriate preventive drug treatment, e.g. isoniazid preventive therapy (IPT).

In patients with active tuberculosis undergoing treatment, there are no good surrogate markers of in vivo bacillary burden. Expectorated bacilli in sputum and bacilli isolated from other disease sites (e.g. pleural fluid or cerebrospinal fluid) represent extracellular bacilli. Although bacilli (whether measured by microscopy, culture, PCR or phage-based assays) gradually disappear from clinical specimens (from disease sites) with effective therapy, these measures are (a) not a good measure of total body bacillary burden and (b) tell us nothing about the remaining intracellular bacterial burden after extracellular bacilli at the disease site have become undetectable.

Conventional immunological assays do not provide a useful surrogate marker of the progress of infection. Antibody responses are not sufficiently dynamic, and stay positive for long after finishing treatment. All cellular immunological assays used to date, actually rise with treatment because of the ill-understood, non-specific immunosuppressive effect of active TB itself.

The invention is a means of monitoring the progress of *M. tuberculosis* infection by sequentially measuring the ex vivo frequency of ESAT-6- specific T cells by ex vivo interferon-γ ELISPOT assay. When patients with active tuberculosis or healthy contacts with latent infection undergo effective anti-tuberculous drug treatment in vivo bacterial load decreases progressively. After 6–9 months of treatment, it is believed that, in the vast majority of individuals (>95%), all remaining intracellular bacilli have been killed, since these individuals very rarely relapse to develop tuberculosis again (unless they acquire exogenous reinfection). Longitudinal follow-up of patients with active tuberculosis and healthy contacts with latent *M. tuberculosis* infection during anti-tuberculous drug treatment, shows that the frequency of ESAT-6-specific T cells measured ex vivo, unlike other cellular immune responses, actually declines progressively with increasing duration of therapy. After completion of therapy, ESAT-6-specific T cells measured ex vivo, are undetectable in most cases (this potentially offers a means of determining whether mycobacterial infection has been eradicated by an intervention). By comparison, the decay kinetics of ESAT-6-specific T cells in patients receiving $2^{nd}$ and $3^{rd}$ line antibiotics for multidrug resistant TB, were slower, and correlated with delayed conversion of sputum to culture negativity (and patients with multidrug resistant TB have a much slower clinical and bacteriological improvement).

The decline in ESAT-6-specific T cells with effective chemotherapy, which reduces bacterial load by several orders of magnitude, suggests that, within a given individual, the frequency of ESAT-6-specific T cells, as enumerated by the ex vivo ELISPOT, is related to antigen load. In biological systems where the in vivo burden of a pathogen and the corresponding antigen load are measurable, it is recognised that the frequency of antigen-specific T cells enumerated ex vivo, correlates with, and is in part driven by, the antigen load. Although there are no quantitative absolute measures of bacterial or antigen load in TB, they must be directly and closely inter-related, and ex vivo quantitation of ESAT-6-specific T cells thus offers a means for longitudinally tracking changes in *M. tuberculosis* bacterial load within an individual.

Thus, the invention covers the monitoring of the progress of *M. tuberculosis* infection over time by direct ex vivo quantitation of ESAT-6-specific T cells. The data generated to date are all based on the use of the ex vivo ELISPOT assay, but other methods for the ex vivo enumeration of antigen-specific T cells may also be used (e.g. MHC tetramer-peptide complexes, intracellular cytokine staining) in addition, or alternatively.

Thus the inventors have found that after effective treatment is administered to a patient with mycobacterial infection there is a decrease in the level of mycobacterial antigen-specific T cells enumerated directly ex vivo. This is the first time that a decrease in the levels of T cells specific for mycobacterial antigens has been found after the treatment of a mycobacterial infection.

The invention thus provides a means of monitoring the progress of a mycobacterial infection by sequentially measuring the ex vivo frequency of myobacterial antigen specific T cells.

The inventors have also found that individuals with a latent mycobacterial infection have detectable levels of T cells specific for mycobacterial antigens. Thus the detection of these T cells may be used to diagnose latent infection.

Accordingly, the invention provides a method of determining the efficacy of treatment for mycobacterial infection in an individual comprising determining in samples from the individual whether the level of T cells specific for a mycobacterial antigen has decreased after treatment, thereby determining the efficacy of the treatment.

The invention also provides a method of determining the presence of a latent infection in an individual comprising determining in a sample from the individual the presence of T cells specific for a mycobacterial antigen.

The invention additionally provides a method of determining the effect of an intervention on a mycobacterial infection in an individual comprising measuring the effect on the levels of the T cells in samples from the individual, thereby determining the effect of the intervention.

The method of detection of T cells preferably is by directly ex vivo enumeration. The T cells are typically specific for ESAT-6 or CFP10, but may also be specific for any other mycobacterial antigen.

DETAILED DESCRIPTION OF THE INVENTION

Figure 1:
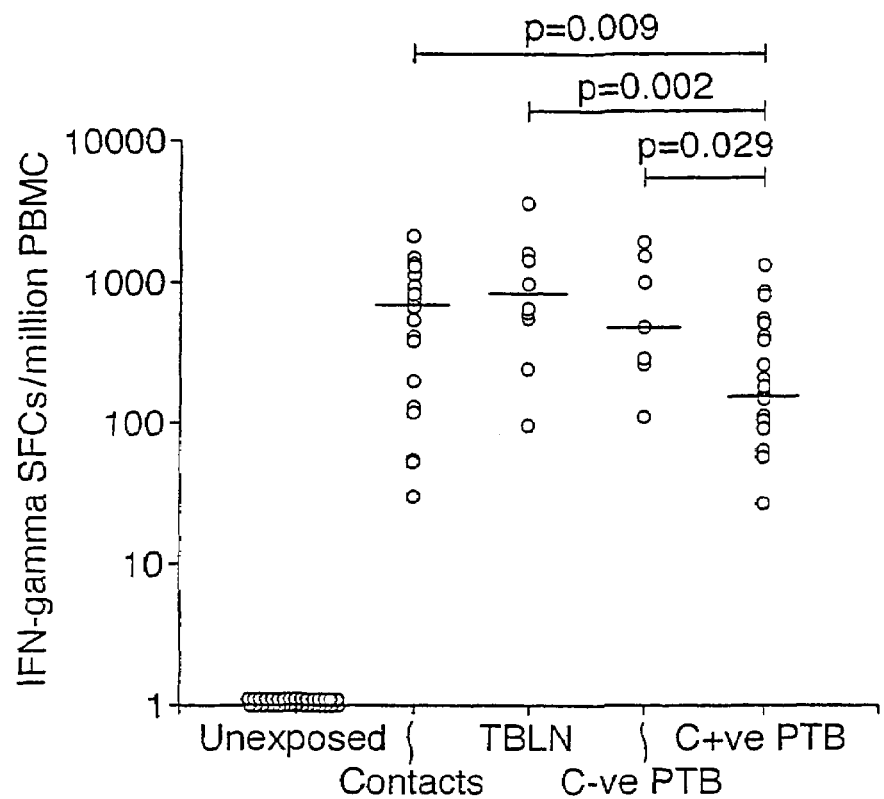
FIG. 1 shows frequencies of ESAT-6 peptide-specific IFN-γ-secreting T cells for the 5 different groups of subjects. Each circle represents an individual subject; the frequency of IFN-γ-secreting T cells to each peptide was summated to give the total number of ESAT-6 peptide-specific T cells. The vast majority of tuberculosis contacts and patients responded (Table 2) and only the responders are represented here. The horizontal bars represent the median frequency of ESAT-6 peptide-specific T cells for each group.

The invention provides a method which can be used to measure in an individual the efficacy of a given treatment or intervention for mycobacterial infection. In the method the effect of a treatment on the level of a particular T cell is detected. The invention also provides a method of diagnosing a latent mycobacterial infection by detecting the presence of the T cell. The invention also provides a method of determining the effect of an intervention on a mycobacterial infection. Herein the term "method" refers to any of these different methods unless the context requires otherwise.

The intervention may be natural or man-made, intentional or unintentional, and may for example be infection by another disease, such as HIV infection or hepatitis B infection.

The method is generally performed on a sample from an individual who is a human or animal, typically an animal which can be naturally or artificially infected by a mycobacterium. Thus the individual may be a mammal, such as a primate, cow, sheep, pig, badger or rodent, e.g. a mouse or rat. The individual typically has an active or latent mycobacterial infection, has had such an infection recently, or is suspected of having a latent mycobacterial infection. The individual may test positive or negative in a Mantoux test. The individual may be at risk of a mycobacterial infection, typically for socio-economic reasons or may have a genetic or acquired predisposition to mycobacterial infection. The individual may be healthy or may have symptoms of a mycobacterial infection.

The individual is generally infected with, or suspected of being infected with, a mycobacterium. The mycobacterium typically expresses ESAT-6 or CFP10, and may be *M. tuberculosis*. The mycobacterium may be *M. marinum* or *M. kansasii*. The pattern of clinical symptoms can be used to distinguish between these two organisms and *M. tuberculosis*. The mycobacterium may be *M. bovis* (which can infect humans).

In the method of determining the efficacy of a treatment the change in level of T cells specific for a mycobacterial antigen is determined by measuring the level of such T cells in a sample from the individual. In order to determine the change in the level of the T cells the level of the T cells in the sample taken after the treatment is administered (referred to herein as the "subsequent sample") is compared to a reference sample taken previously from the same patient.

Typically the reference sample is taken from the patient before the treatment or intervention is administered or before it has had any effect, such as within one or two hours of the treatment being administered. The subsequent sample is typically taken within six months of the treatment administration, such as within a month or 2 weeks of the administration. In the method of detecting the effect of an intervention the sample may be taken at any of the above-mentioned times after the intervention.

The treatment whose efficacy is being determined is typically a new or old treatment. The treatment may be a natural agent such as a vitamin (e.g. vitamin D), mineral or plant-derived product. The treatment may be a preventative or therapeutic vaccine. The treatment is typically isoniazid, rifampicin, ethambutol, pyrazinamide or streptomycin.

If a particular treatment is found to have a low efficacy, i.e. the treatment does not cause a substantial decrease in the level of the T cells then a different treatment may be administered to the individual. The decrease in the level of T cells may be compared with the decrease in the case of a successful treatment. In one embodiment a treatment which has a low efficacy will cause a decrease of a rate of less than 5% (e.g. less than 1%) per week in the levels of the T cells.

The different treatment which is typically administered when a first treatment has low efficacy (for example when bacilli are resistant to the first line drug) may be para-aminosalicyclic acid, kanamyin, capreomycin, ethionamide, cycloserine, thiacetazone or a fluorpuinolone (e.g. ciprofloxacin).

In certain individuals the T cell levels may decrease after treatment and then remain detectable at a substantially constant level, say over the period of at least two months. This may indicate the change of the infection from an active one to a latent one, unless re-exposure to a mycobacterium occurs whereupon the level of the T cells may rise.

Typically in the method of determining the presence of a latent mycobacterial infection the detection of a frequency of at least 20 T cells specific for ESAT-6 or 20 T cells specific for CFP-10 per million peripheral blood mononuclear cells (PBMCs) may be taken to indicate the presence of a latent infection. The frequency of these cells would be expected to remain relatively constant in an individual with an untreated latent infection.

The T cells which are detected in the method recognize a mycobacterial protein antigen. Thus the T cells will be specific for/bind to peptides from that protein, i.e. will be specific for/bind to particular fragments (or epitopes) of the protein. Typically the T cells are specific for peptides from ESAT-6 or CFP-10. The T cells may be CD4 or CD8 T cells. The T cells have been pre-sensitized in vivo to the mycobacterial proteins, and may be present in the peripheral blood of an individual which has been exposed to the mycobacterium at a frequency of 1 in $10^6$ to 1 in $10^3$ PBMCs.

In a preferred embodiment the level of, or presence of, T cells is detected by contacting cells of the sample with (i) a whole myobacterial protein, or (ii) a peptide which is a fragment of a mycobacterial protein, or (iii) an analogue of (i) or (ii) which is recognized by a T cell receptor that recognises (i) or (ii). Thus the peptide sequence which is recognized may be a fragment of ESAT-6 or CFP-10.

The sequence which is recognized is at least 8 amino acids in length, typically at least 12, 15, 20 or more amino acids in length.

The peptide which is used in the method is thus typically a peptide which has or comprises a sequence which is the same as the fragment of ESAT-6 or CFP-10 referred to above, e.g. a fusion protein. The peptide typically has a length of at least 8, 10, 15, 20 or more amino acids, and typically has a length of less than 100 amino acids, such as less than 80 or less than 60 amino acids.

Determination of whether the T cells recognize the peptide is generally done by detecting a change in the state of the T cells in the presence of the peptide or determining whether the T cells bind the peptide. The change in state is generally caused by antigen specific functional activity of the T cell after the T cell receptor binds the peptide. Generally when binding the T cell receptor the peptide is bound to an MHC class I or II molecule, which is typically present on the surface of an antigen presenting cell (APC).

The chance in state of the T cell may be the start of or increase in secretion of a substance from the T cell, such as a cytokine, especially IFN-γ, IL-2 or TNF-α. Intracellular changes may be detected, for example by using intracellular staining techniques, typically intracellular cytokine staining (e.g. for any of the cytokine mentioned herein). After such staining the staining can be detected using a cell sorting technique, for example using a FACS technique.

Determination of IFN-γ secretion is particularly preferred. The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilized on a solid support. In one embodiment this allows the actual number of responding T cells to be determined since after binding the agent the substance will remain in the vicinity of the T cell which secreted it. Thus 'spots' of substance/agent complex may form on the support, each spot representing a T cell which is secreting the substance. Quantifying the spots (and typically comparing against a control) allows determination of recognition of the peptide.

After the substance is allowed to bind the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody which is immobilized on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below.

Generally the T cells which are contacted in the method are taken from the individual in a blood sample, although other types of body sample which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD4 T cells, can be purified from the sample. PBMCs, MCs and T cells can be separated from the sample using techniques known in the art, such as those described in Lalvani et al (1997) *J. Exp. Med.* 186, p859–865.

Preferably the T cells which are detected are in the form of unprocessed or diluted samples. The T cells are preferably directly ex vivo, i.e. they are not cultured before being used in the method. The T cells are typically freshly isolated T cells (such as in the form of freshly isolated MCs or PBMCs).

The APC which is typically present in the method be isolated may from the same individual as the T cell or from a different individual. The APC may be a naturally occurring APC or an artificial APC. The APC is a cell which is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalized cell line. The APC may express empty MHC class II molecules on its surface.

In the method one or more peptides (typically at least 2, 5, 10 or more different peptides) may be used. Thus the T cells can be placed into an assay with all the peptides (i.e. a pool of the peptides) which it is intended to test. Alternatively the T cells can be divided and placed into separate assays each of which contain some of the peptides which it is intended to test.

In one embodiment peptide per se is added directly to an assay comprising T cells and APCs. As discussed above the T cells and APCs in such an assay could be in the form of MCs. When peptides which can be recognized by the T cell without the need for presentation by APCs are used then APCs are not required. Analogues which comprise or mimic the original peptide bound to a MHC molecule are an example of such a peptide.

In one embodiment the peptide is provided to the APC in the absence of the T cell. The APC is then provided to the T cell, typically after being allowed to present the peptide on its surface. The peptide may have been taken up inside the APC and presented, or simply be taken up onto the surface without entering inside the APC.

The duration for which the peptide is contacted with the T cells will vary depending on the method used for determining recognition of the peptide. Typically $10^5$ to $10^7$, preferably $5\times10^5$ to $10^6$ PBMCs are added to each assay. In the case where peptide is added directly to the assay its concentration is generally from $10^{-1}$ to $10^3$ µg/ml, preferably 0.5 to 50 µg/ml or 1 to 10 µg/ml.

Typically the length of time for which the T cells are incubated with the peptide is from 4 to 24 hours, preferably 6 to 16 hours. When using ex vivo PBMCs it has been found that $0.3\times10^6$ PBMCs can be incubated in 10 µg/ml of peptide for 12 hours at 37° C.

In the method instead of the peptide(s) an analogue may be used which is recognized by the T cell receptor that recognizes the peptide. Therefore generally when the analogue is added to T cells in the presence of the equivalent said peptide, typically also in the presence of an APC, the analogue inhibits the recognition of the equivalent peptide. The binding of the analogue to the said T cell receptors can be tested by standard techniques. For example T cell receptors can be isolated from T cells which have been shown to recognize the peptide (e.g. using any of the detection of recognition assays discussed above). Demonstration of the binding of the analogue to the T cell receptors can then shown by determining whether the T cell receptors inhibit the binding of the analogue to a substance that binds the analogue, e.g. an antibody to the analogue. Typically the analogue is bound in an MHC class II molecule in such an inhibition of binding assay.

Typically the analogue inhibits the binding of the peptide to a T cell receptor. In this case the amount of peptide which can bind the T cell receptor in the presence of the analogue is decreased. This is because the analogue is able to bind the T cell receptor and therefore competes with the peptide for binding to the T cell receptor.

T cells for use in the above binding experiments can be isolated from patients with mycobacterial infection.

Other binding characteristics of the analogue are also the same as the peptide, and thus typically the analogue binds to the same NBC class II molecule which the peptide binds. The analogue typically binds to antibodies specific for the peptide, and thus inhibits binding of the peptide to such an antibody.

The analogue is typically a peptide. It may have homology with the equivalent original peptide. A peptide which is homologous to another peptide is typically at least 70% homologous to the peptide, preferably at least 80 or 90% and more preferably at least 95%, 97% or 99% homologous thereto, for example over a region of at least 15, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology"). For example the UWGCG Package provides the BESTFIT program which can be used to calculate homology (for example used on its default settings) (Devereux et al (1984) *Nucleic Acids Research* 12, p387–395).

An analogue which is a peptide typically has any of the amino acid lengths mentioned above for the peptide discussed above. Typically the amino acids in the analogue at the equivalent positions to amino acids in the original peptide which contribute to binding the MHC molecule or are responsible for the recognition by the T cell receptor, are the same or are conserved.

Typically the analogue peptide comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The analogue may comprise one or more non-natural amino acids, for example amino acids with a side chain different from natural amino acids. Generally, the non-natural amino acid will have an N terminus and/or a C terminus. The non-natural amino acid may be an L- or D-amino acid. The analogue typically has a shape, size, flexibility or electronic configuration which is substantially similar to the original peptide. It is typically a derivative of the original peptide.

In one embodiment the analogue is or mimics the original peptide bound to a MHC class I or II molecule. The analogue may be or may mimic the original peptide bound to 2, 3, 4 or more MHC class I or II molecules associated or bound to each other. These MHC molecules may be bound together using a biotin/streptavidin based system, in which typically 2, 3 or 4 biotin labelled MHC molecules bind to a streptavidin moiety. This analogue typically inhibits the binding of the peptide/MHC Class I or II complex to a T cell receptor or antibody which is specific for the complex. The analogue is typically an antibody or a fragment of an antibody, such as a Fab or $(Fab)_2$ fragment.

The analogue may be immobilized on a solid support, particularly an analogue which mimics peptide bound to a MHC molecule.

The analogue is typically designed by computational means and then synthesized using methods known in the art. Alternatively the analogue can be selected from a library of compounds. The library may be a combinatorial library or a display library, such as a phage display library. The library of compounds may be expressed in the display library in the form of being bound to a MHC class I or II molecule, such as the MHC molecule which the original peptide binds. Analogues are generally selected from the library based on their ability to mimic the binding characteristics of the original peptides. Thus they may be selected based on ability to bind a T cell receptor or antibody which recoanizes the original peptide.

In one embodiment the T cells are detected not based on their response to a substance but based on their ability to bind a specific binding agent. Typically the agent is or comprises any of the proteins, peptides or analogues mentioned herein. The agent may be labelled (for example using any of the detectable labels mentioned herein). The specific binding agent may comprise an ARC molecule, and is preferably an MHC tetramer-peptide complex (for example as mentioned above).

The peptide or analogue discussed herein can be made using standard synthetic chemistry techniques, such as by use of an automated synthesizer. They can be made from a longer polypeptide, e.g. a fusion protein, which polypeptide typically comprises the sequence of the peptide, and may be derived from the polypeptide by for example hydrolyzing the polypeptide, such as using a protease; or by physically breaking the polypeptide. The polypeptide is typically ESAT-6 or CSF-10, which may have been expressed recombinantly.

The therapeutic agents mentioned herein may be in the form of a pharmaceutical composition which comprises the agent and a pharmaceutically acceptable carrier or diluent. Suitable carriers and diluents include isotonic saline solutions, for example phosphate-buffered saline. Typically the agent is administered by parenteral, intravenous, intramuscular, subcutaneous, transdermal, intradermal, oral, intranasal, intravaginal, or intrarectal administration.

The dose of agent may be determined according to various parameters, especially according to the particular agent; the age, weight and condition of the patient to be treated; the route of administration; and the required regimen. A physician will be able to determine the required route of administration and dosage for any particular patient. A suitable dose may however be from 10 µg to 10 g, for example from 100 µg to 1 g of the agent.

The invention is illustrated by the following Examples:

EXAMPLE 1

The Detection of the Correlation Between CD4 T cell Levels and Bacterial Load Methods Subjects Adult patients and contacts were recruited prospectively from London and Oxford. A heparinized blood sample was drawn from all participants. No subjects had features of HIV infection and patients known to be HIV infected were excluded. Demographic characteristics are shown in Table 1.

27 healthy household contacts (HHC) were recruited on the basis of the following criteria. All had lived in the same household as an index case of untreated sputum smear positive pulmonary tuberculosis within the last 6 months, were asymptomatic and had normal chest radiography. In addition, all HHCs had strongly positive TSTs (Heaf grade 3 or 4), which was performed by standardized multiple puncture tuberculin skin testing with a 6 needle disposable head Heaf gun (Bignall 2000, Bignall Surgical Instruments, UK) and concentrated purified protein derivative (PPD) 100,000 tuberculin units/ml (Evans Medical, Liverpool, UK) in accordance with UK guidelines for evaluation of tuberculosis contacts. 23 HHCs had been BCG-vaccinated and none developed tuberculosis over a 12 month period of follow up. None had received chemoprophylaxis at the time of venipuncture.

32 healthy unexposed controls (UC) with no history of tuberculosis and no known tuberculosis contact were recruited prospectively. Most were laboratory staff and 28 had been BCG-vaccinated.

25 patients with culture positive PTB (C+PTB) had clinical and radiographic findings consistent with tuberculosis and positive cultures for *M. tuberculosis* from one or more respiratory specimens. 18/25 (72%) PTB patients had received either no therapy, or less than 4 weeks therapy at the time of venepuncture.

8 patients with culture negative PTB (C−PTB) had a clinical diagnosis made on the basis of highly suggestive appearances on chest radiography and positive tuberculin skin tests. All were asymptomatic and had no previous history of treatment for tuberculosis. All respiratory samples, which consisted of 3 sputum specimens (or 3 gastric washings in the absence of productive cough) and a bronchoalveolar lavage for each patient, were negative for *M. tuberculosis* culture. 6/8 (75%) of this group had received either no therapy, or less than 4 weeks therapy.

11 patients with tuberculous lymphadenitis (TBLN) had consistent clinical findings, positive TSTs and a good response to anti-tuberculous chemotherapy. 7 had lymph node biopsies of which 5 grew *M. tuberculosis* on culture. 5/11 (45%) TBLN patients had received either no therapy, or less than 4 weeks therapy at the time of venipuncture.

Seventeen patients with non-lymph node extrapulmonary tuberculosis (EPTB) were recruited on the basis of clinical findings and positive cultures for *M. tuberculosis* from one or more clinical specimens. 4 patients had tuberculosis osteomyelitis, 2 had musculoskeletal tuberculosis (psoas abscess), 4 had pleural disease, 3 had miliary disease, 3 had abdominal disease and 1 had meningitis. The small number of patients precluded statistical comparisons of T cell frequencies between the subgroups of EPTB.

Peptides 17 peptides spanning the length of the ESAT-6 molecule were synthesized by solid-phase Fmoc chemistry (Research Genetics, Alabama, USA). Each peptide was 15 amino acids in length and overlapped its adjacent peptide by 10 residues. Identity was confirmed by mass spectrometry and purity by high performance liquid chromatography. Sequence homology searches of the SwissProt and translated GenBank protein databases confirmed that these peptides are uniquely restricted to the ESAT-6 protein of *M. tuberculosis* complex.

Ex Vivo ELISPOT Assay for Single Cell IFN-γ Release: Enumeration of Circulating ESAT-6 Peptide-specific T Cells from Peripheral Blood PBMC were separated from 20 mls blood by standard means and suspended in RPMI supplemented with 2 mM L-glutamine, 100 µg/ml ampicillin, 50 µg/ml gentamicin, 1 mM sodium pyruvate and 10% heat-inactivated foetal calf serum (Sigma, St. Louis, Mo., USA) (R10). As previously described (1,2), 96-well PVDF-backed plates (MAIPS45, Millipore, Bedford, Mass., USA), pre-coated with 15 µg/ml of anti-IFN-γ mAb 1-D1K (Mabtech, Stockholm, Sweden), were blocked with R10 for 2 h. 3×10⁵ PBMC were added in 100 µl R10/well and peptides added individually to single wells at 10 µg/ml. PPD (Batch RT49, Statens Seruminstitut, Copenhagen, Denmark) was also tested at 20 µg/ml. Phytohaemagglutinin (PHA) (ICN Biomedicals, Aurora, Ohio, USA) at 5 µg/ml was added to duplicate positive control wells and no peptide to duplicate negative control wells. Recombinant ESAT-6 was added to single wells at 10 µg/ml for 35 subjects.

After 14 h incubation at 37° C., 5% $CO_2$ plates were washed with PBS 0.050% Tween-20 (Sigma St. Louis, Mo., USA). 50 µl of 1 µg/ml of biotinylated anti-IFN-γ mAb, 7-B6-1-biotin (Mabtech), was added. After 2 h, plates were washed and streptavidin-alkaline phosphatase conjugate (Mabtech) was added to 1:1000. After 1 h and further washing, 50 µl of diluted chromogenic alkaline phosphatase substrate (Biorad, Hercules, Calif., USA) was added. After 20 mins plates were washed and allowed to dry.

ELISPOT Assay for Single Cell IL-4 Release

These assays were carried out as described above using high affinity IL-4-specific antibodies (IL-4-I catcher and biotinylated IL-4-II detector (Mabtech)) and a 60 h incubation period.

Enumeration of IFN-γ Spot-forming Cells (SFCs)

IFN-γ SFCs were counted using a magnifying glass and responses were scored as positive if test wells contained at least 5 IFN-γ SFCs more than negative control wells and this number was at least twice that in negative control wells. This pre-defined cut-off of 5 IFN-γ SFCs per 3×10⁵ PBMC for a positive result translates into a detection threshold of 17 specific T cells per million PBMC, or 1/59,000 PBMC. The person performing and reading the assays was blinded to the clinical status of the different groups of patients and HHCs, but not to the UCs. Background numbers of SFCs in negative control wells were below 5. After subtraction of background values, the number of IFN-γ SFCs specific for each peptide was summated and this total number of ESAT-6 peptide-specific SFCs for a given individual was used for comparisons between groups of subjects and between different time points during treatment of individual patients.

In Vitro Generation of Peptide-specific T Cell Lines

T cell lines were generated as previously described (2). Briefly, PBMC were suspended at 5×10⁵ cells/ml in AB medium (RPMI supplemented with L-glutamine 2 mM, ampicillin 100 µg/ml, gentamicin 5 µg/ml and 10% heat-inactivated pooled human AB serum {National Blood Transfusion Service, Bristol, UK}) and 200 µl were added per well in a round-bottomed 96-well plate. Peptide was added at 10 µg/ml. 10 U/ml IL-2 in the form of Lymphocult-T (Biotest, Dreieich, Germany) was added every 3 days. After 12 days, T cell lines were immunomagnetically depleted and tested against the stimulating peptide in duplicate wells in ELISPOT assays for IFN-γ using 1–5×10⁴ cells/well.

Immunomagnetic Cell Depletions

CD4 and CD8 T cells were depleted from T cell lines by 30 mins incubation with anti-CD4 or anti-CD8 ribs conjugated to ferrous beads at a ratio of 10 beads to 1 cell using Dynabeads M-450 (Dynal, Oslo, Norway) in 200 µl R10 on ice. Following dilution in R10, the conjugate-coated cells were removed by a magnet (Dynal, Oslo, Norway). These Dynabeads reliably deplete >99% of the target cell population.

³H-thymidine Incorporation Lymphoproliferation Assays

2×10⁵ PBMC were seeded per well in 200 µl AB medium in 96-well round-bottomed plates. Peptides were added at 10 µg/ml, negative control wells had medium only and positive control wells contained PPD at 20 µg/ml. All conditions were set up in triplicate wells. Following incubation at 37° C., 5% $CO_2$ for 5 days, 1 µCi ³H-thymidine was added to each well. After 18 h, wells were harvested and ³H-thymidine incorporation measured in a β-counter (Wallac, UK). Results were scored as positive if the stimulation index was 3 or more.

Inhibition of T Cell Responses in ELISPOT Assays with Anti-MHC Class II Antibodies HLA class II restriction of the CD4 T cell response to two immunodominant peptides ESAT-6$_{1-15}$ and ESAT-6$_{71-85}$, was investigated using T cell lines as well as ex vivo PBMC. The murine monoclonal antibodies L243, L2 and B7.21, that block peptide presentation to CD4 T cells by HLA-DR, -DQ and -DP, respectively, were added at 10 µg/ml to 3 separate pairs of duplicate wells in ELISPOT assays followed by 10 µg/ml peptide 90 mins later. Control duplicate wells received peptide only, or neither peptide nor antibody Statistical Methods Summated frequencies of ESAT-6-peptide-specific IFN-γ SFCs for responders were compared between patient groups using the non-parametric Mann-Whitney test (2-tailed) and between the first and last time points sampled in the treatment course of individual patients using the non-parametric Wilcoxon Signed Rank test (2-tailed). The proportional decrease in antigen-specific T cell frequencies during therapy was calculated using the Student's t test on log transformed data.

EXAMPLE 2

Frequencies of ESAT-6 Specific T Cells

It was found that ESAT-6 peptide-specific IFN-γ-secreting CD4 T cells circulate at high frequencies in *M. tuberculosis*-infected individuals and correlate with clinically defined protective immunity. Such T cells were detected in almost all tuberculosis patients and the majority of contacts. Responses were observed in 10/11 TBLN patients, 7/8 C–PTB patients, 23/25 C+PTB patients and 23/27 HHCs (Table 1). It is possible that the 4 HHCs who did not respond to ESAT-6 were not infected with *M. tuberculosis;* their positive TSTs may have resulted from prior BCG vaccination. By contrast, none of the 32 UCs (of whom 28 were BCG-vaccinated) responded to ESAT-6 peptides in the ex viva ELISPOT assay for IFN-γ (Table 1), consistent with ESAT-6-specific responses being *M. tuberculosis*-specific. Frequencies of ESAT-6 peptide-specific IFN-γ-secreting T cells for all responders from each group are shown in FIG. 1 and summarized in Table 1. For the HHCs that responded to ESAT-6 (n=23), frequencies of ESAT-6-specific T cells were significantly higher (p=0.009) than among the C+PTB patients who responded (n=23) and higher (p=0.044) than the PTB (C+ and C–) group as a whole (n=30). Both groups of ESAT-6-responsive patients with minimal, paucibacillary disease, TBLN (n=10) and C–PTB (n=7), also had significantly higher frequencies of ESAT-6 peptide-specific T cells than the C+PTB patients (p=0.002 and p=0.029, respectively).

Figure 2:
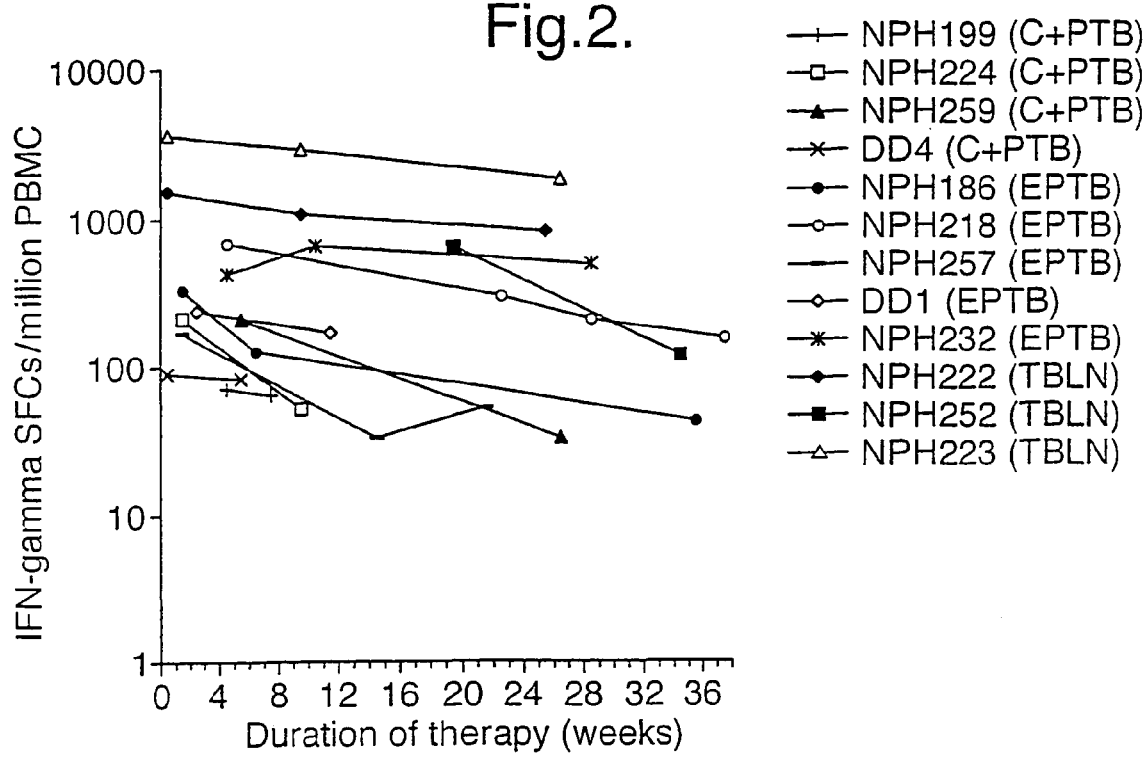
FIG. 2 shows frequencies of ESAT-6 peptide-specific IFN-γ-secreting T cells decline with anti-tuberculous chemotherapy (p=0.005; n=12). The summated number of ESAT-6 peptide-specific T cells for each patient, enumerated by ex vivo ELISPOT, is shown at various time points during the course of therapy. The overall frequency of ESAT-6 peptide-specific IFN-γ-secreting T cells fell, on average, by a factor of 0.62 (95% CI: 0.37–0.76) (that is, to 38% of the initial values) over the time period shown. The average rate of decay was 5.5% (95% CI: 2.4–8.4) per week. This decline was observed for all groups of patients followed up: C+PTB (culture positive pulmonary tuberculosis: n=4); TBLN (tuberculous lymphadenitis: n=3) and EPTB (extrapulmonary tuberculosis: military, n=1; pleural, n=2, osteomyelitis, n=1). For one EPTB patient (NPH232: military), the T cell frequency initially rose, then declined.
Figure 2:
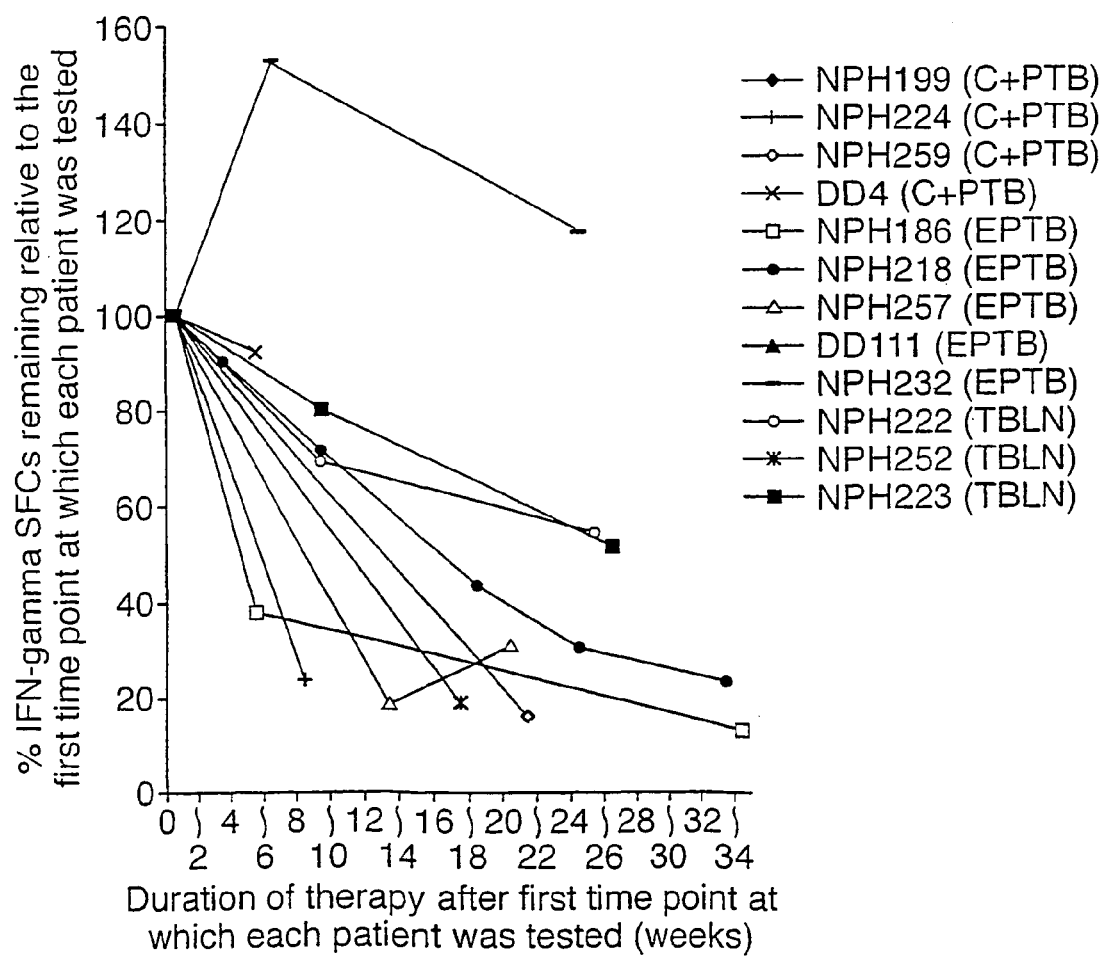

It was also observed that frequencies of circulating ESAT-6-specific IFN-γ-secreting T cells in tuberculosis patients decline progressively with treatment. If lower frequencies of ESAT-6-specific IFN-γ-secreting T cells in patients with active C PTB were a result of non-specific disease-associated immunosuppression, T cell frequencies would be expected to rise during effective treatment. We therefore longitudinally tracked 12 patients (4 C+PTB, 3 TBLN and 5 EPTB) on anti-tuberculous chemotherapy and observed a decline in the overall frequency of ESAT-6 peptide-specific T cells (p=0.005) (FIG. 2). The average decrease over the mean follow-up period of 18.6 weeks was by a factor of 0.62 (95% CI: 0.37–0.76), that is, to 38% of the initial values, and the rate of decay was 5.5% (95% CI: 2.4–8.4) per week. The frequencies of T cells specific for each of the peptides declined in parallel but only the summated responses to all ESAT-6-derived peptides are shown for clarity.

Figure 3:
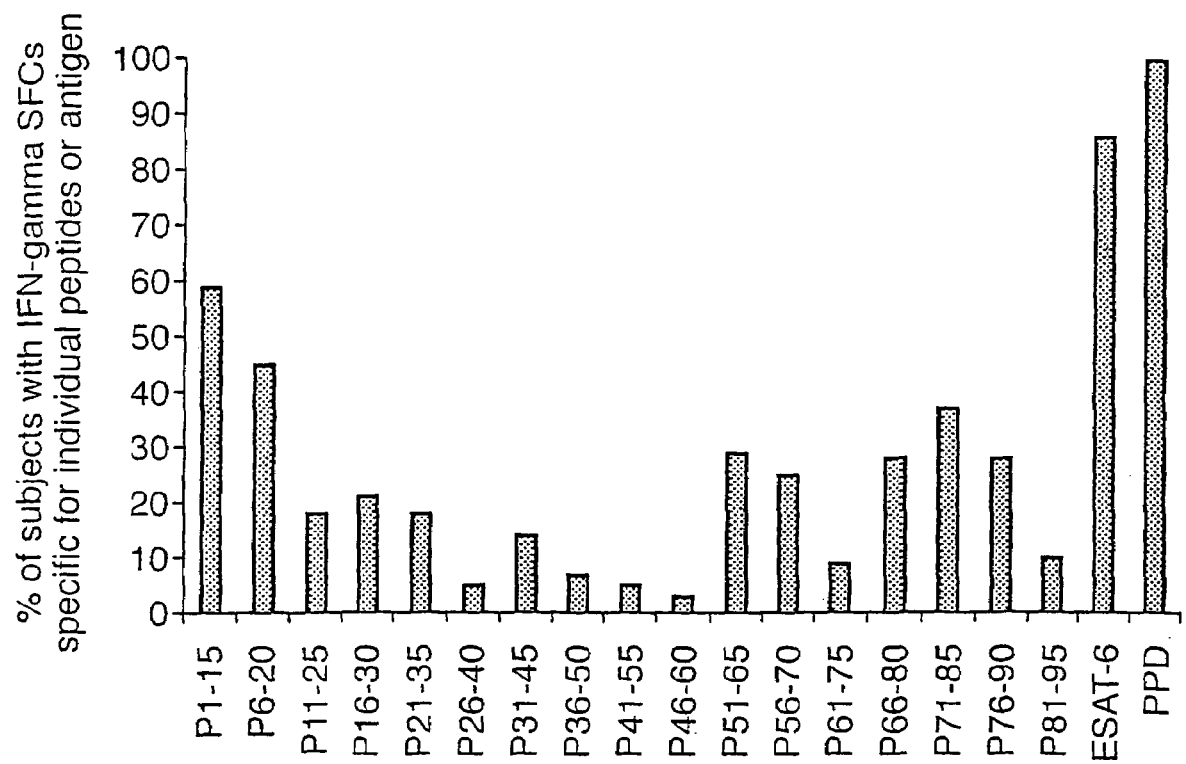
FIG. 3 shows CD4 epitope map of ESAT-6 as defined by ex vivo peptide-specific IFN-γ ELISPOT responses for all 88 tuberculosis patients and contacts. The percentage of subjects that responded to each peptide is shown, and in each case 88 subjects were tested against each peptide. For rESAT-6 antigen, 35 tuberculosis patients and contacts were tested.

Using the ex viva ELISPOT assay, each of the overlapping ESAT-6-derived 15mer peptides was recognized by IFN-γ-secreting T cells from one or more of 88 tuberculosis patients and contacts tested (FIG. 3). In this population, peptides $ESAT-6_{1-15}$, $ESAT-6_6-20$ and $ESAT-6_{71-85}$ are particularly widely recognized, by 59%, 45% and 37% of subjects respectively.

59 T cell lines were generated from several patients and HHCs against 15 ESAT-6-derived peptides after 12 days culture with IL-2 supplementation, ELISPOT assays were performed before and after immunomagnetic depletion of CD4 or CD8 T cells. For 55/59 T cell lines, peptide-specific responses were abrogated by CD4 depletion (Table 2); 4 T cell Lines specific for certain peptides were CD8 positive (2, 3).

A response in the ex vivo ELISPOT assay for IFN-γ indicates T cell-mediated IFN-γ-secretion within 14 h of exposure to peptide. To establish how quickly these T cells can release IFN-γ upon antigen encounter, we carried out 6 h ex vivo ELISPOT assays in 3 subjects (2 HHCs and 1 C–PTB) with 11 peptides. In each case, IFN-γ SFCs were readily detected at 6 h to all the peptides that gave a response at 14 h. The frequency of peptide-specific IFN-γ-secreting T cells enumerated at 6 h was 80–90% of that at 14 h, (data not shown), indicating that ESAT-6 peptide-specific T cells are capable of rapid effector function (1).

Using PBMC from 15 subjects, lymphoproliferation assays were performed in parallel to ex vivo IFN-γ ELISPOT assays using 16 different peptides. Surprisingly, we did not detect proliferation to peptides $ESAT-6_{1-15}$ and $ESAT-6_{71-85}$ in several subjects with IFN-γ-secreting T cells specific for these peptides in the ex vivo ELISPOT (Table 2). 12 subjects responded to $ESAT-6_{1-15}$ by en vivo ELISPOT (mean peptide-specific IFN-γ SFCs for responders: $77/10^6$ PBMC [IQ range: 38–100]) compared with only 3 by lymphoproliferation. For $ESAT-6_{71-85}$, 10 subjects responded by ex vivo ELISPOT (mean peptide-specific IFN-γ SFCs for responders: $121/10^6$ PBMC [IQ range: 65–171]) compared with 5 by lymphoproliferation. However, lymphoproliferative responses to the positive control, PPD, were strong: mean stimulation index: 82 (IQ range: 35–98). Nonetheless, peptide-specific T cell lines were readily generated by peptide stimulation in vitro with IL-2 supplementation; thus, these ESAT-6 peptide-specific T cells, while displaying rapid effector function upon antigen contact, cannot proliferate in vitro in the absence of exogenous IL-2. For several other peptides, however, there was a broad concordance between the two assays (Table 2).

EXAMPLE 3

HLA Restriction of $ESAT-6_{1-15}$ $ESAT-6_{71-85}$

Figure 4A:
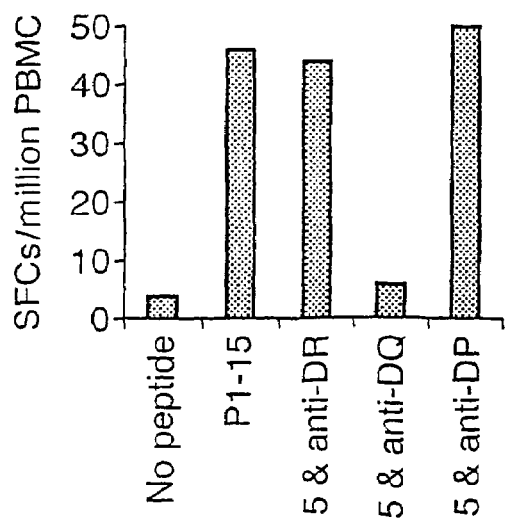
FIG. 4 shows CD4 T cell responses to the immunodominant epitopes $ESAT-6_{1-15}$ and $ESAT-6_{71-85}$ are HLA-DQ-restricted. IFN-γ SFCs specific for peptides $ESAT-6_{1-15}$ (FIGS. 4A–C) and $ESAT-6_{71-85}$ (FIGS. 4D, E) are markedly diminished by anti-HLA-DQ antibody but not by antibodies to HLA-DR or HLA-DP. For $ESAT-6_{1-15}$, results are shown for ex vivo PBMC from healthy contact NPH209 (4A), $ESAT-6_{1-15}$-specific T cell line from healthy contact GM19 (4B) and $ESAT-6_{1-15}$-specific T cell line from TBLN patient NPH223 (4C). For $ESAT-6_{71-85}$, results are shown for ex vivo PBMC from healthy contact GM19 (4D) and $ESAT-6_{71-85}$-specific T cell line from TBLN patient NPH223 (4D). In each case, the frequency of IFN-γ SFCs shown is the mean for two duplicate wells.
Figure 4B:
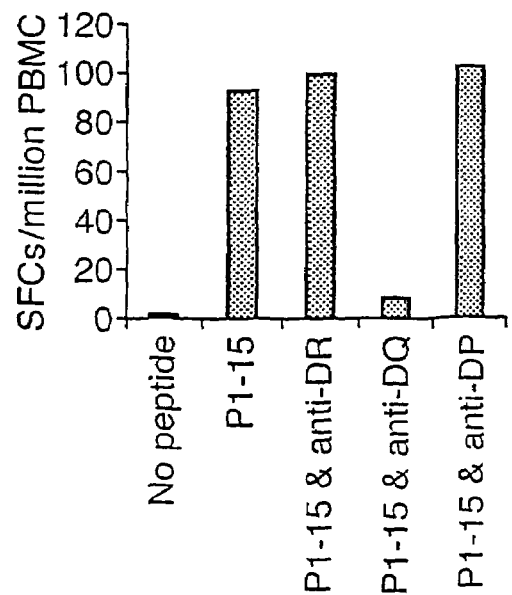
Figure 4C:
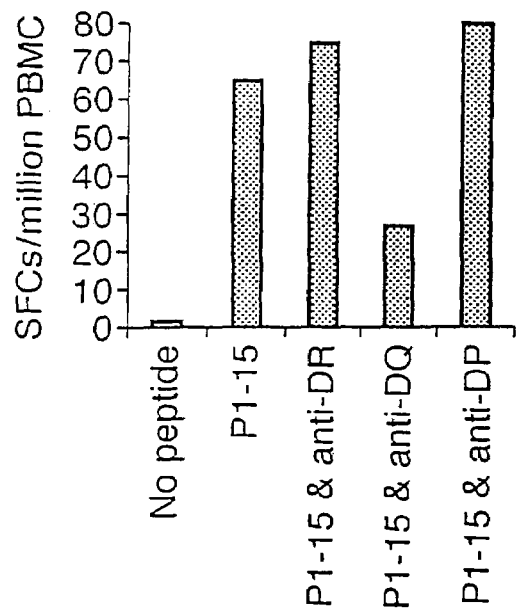
Figure 4D:
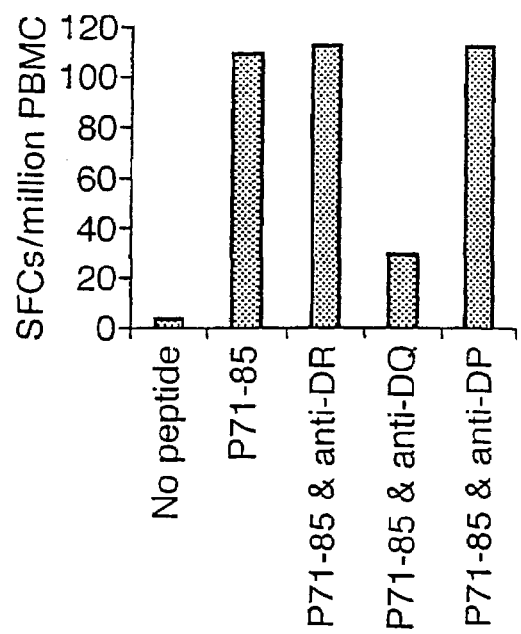
Figure 4E:
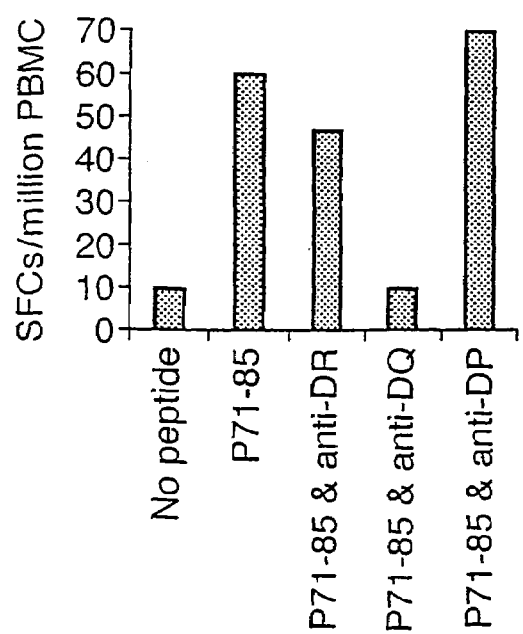

We were interested to determine the MHC restriction of the two peptides that were immunodominant by ex vivo ELISPOT but gave discrepant results in lymphoproliferation assays. We used monoclonal antibodies to block presentation of peptide to T cell lines and ex vivo PBMC in ELISPOT assays. For $ESAT-6_{1-15}$, in all 3 individuals tested, IFN-γ SFCs were markedly diminished by anti-HLA-DQ antibody but not by antibodies to HLA-DR or -DP (FIGS. 4A–C). For $ESAT-6_{71-85}$, 2 individuals were tested, and in both cases, the response was blocked only by the anti-HLA-DQ antibody (FIGS. 4D, E). In contrast, ex vivo ELISPOT responses to the other peptides tested ($ESAT-6_{6-20}$, $ESAT-6_{51-65}$, $ESAT-6_{66-80}$ and $ESAT-6_{76-90}$) were shown to be HLA-DR-restricted (data not shown).

EXAMPLE 4

Further Characterization of the ESAT-6 Specific T cells

In 35 subjects (28 patients and 7 HHCs) rESAT-6 antigen was tested in the ex vivo ELISPOT assays in parallel with ESAT-6 peptides and 30/35 (86%) responded to rESAT-6 (FIG. 3). The 5 subjects who did not respond to the protein were subjects who also failed to respond to any of the 17 peptides. Thus, of 30 patients who responded to one or more peptides, all responded to rESAT-6 antigen, indicating that rESAT-6 is processed and presented to T cells in the ex vivo ELISPOT assay.

Freshly isolated PBMC from 10 tuberculosis patients (5 C+PTB and 5 EPTB) and 8 HHCs were tested ex vitro against all 17 ESAT-6 derived peptides in an ELISPOT assay for IL-4 in parallel with the ELISPOT assay for IFN-γ. The numbers of SFCs were summated for each peptide. Among the tuberculosis patients 10/10 had ESAT-6 peptide-specific IFN-γ-secreting T cells (mean: 668 IFN-γ SFCs/million PBMC) while 0/10 had ESAT-6 peptide-specific IL-4-secreting T cells. For the HHCs, 6/8 responded in the IFN-γ ELISPOT assay (mean frequency in responders: 414 ESAT-6 peptide-specific IFN-γ SFCs/million PBMC) compared with 2/8 responders in the IL-4 ELISPOT assay (mean frequency in responders: 93 ESAT-6 peptide-specific IFN-γ SFCs/million PBMC). Positive controls for IFN-γ and IL-4 ELISPOT assays with PHA stimulation were always over 500 IFN-γ or IL-4 SFCs per $10^6$ PBMC, respectively.

Discussion

By direct ex vivo analysis, we have identified a population of antigen-specific IFN-γ-secreting CD4 T cells that circulate in the blood of almost all *M. tuberculosis*-infected individuals, but are absent in unexposed, BCG-vaccinated controls. The presence of high frequencies of circulating IFN-γ-secreting ESAT-6-specific CD4 T cells in PPD-positive recently exposed HHCs, who were clinically and radiographically free of disease, indicates that these T cells are not necessarily associated with tissue pathology per se. Rather, their presence in these individuals may be consistent with a role in the containment of *M. tuberculosis* in vivo. This hypothesis is supported by the observation that ESAT-6-specific CD4 T cells circulate at higher frequencies in HHCs than in C+PTB patients (FIG. 1). Amongst subgroups of tuberculosis patients, the frequency of these T cells was higher in those groups who manifest relatively more successful containment of *M. tuberculosis* in Thus TBLN patients (with highly localised disease, minimal symptoms and frequent spontaneous resolution) and C−PTB patients (with no symptoms and no evidence of ongoing bacterial replication in multiple clinical specimens) both had higher frequencies of ESAT-6-specific CD4 T cells than C+PTB patients with *M. tuberculosis* actively growing in respiratory secretions (Table 1 and FIG. 1). Thus, the overall frequency of ESAT-6-specific IFN-γ-secreting CD4 T cells appears to correlate with clinically-defined protective immunity.

However, active tuberculosis causes an ill-defined non-specific immunosuppression. It is therefore possible that immune responses that are weaker in patients with more extensive active disease than in patients with minimal disease, are merely secondarily suppressed as a consequence of active tuberculosis itself. If this where the case, immune responses should rise with treatment and, in general, antigen-specific or PPD-specific IFN-γ secretion in PBMC bulk cultures and lymphoproliferative responses do increase during anti-tuberculous therapy. Thus, previously identified associations of stronger T cell responses with minimal disease did not correlate with protective immunity because the weaker responses in patients with more extensive disease recover with treatment. It has therefore not been possible to identify correlates of clinically defined protective immunity based on these conventional assays. However, longitudinal follow up of tuberculosis patients with the en vivo ELISPOT assay showed that the frequency of ESAT-6 specific IFN-γ-secreting CD4 T cells actually fell during therapy (p=0.005) (FIG. 2). This indicates that the lower frequency of ESAT-6-specific T cells in patients with more extensive disease is not a secondary effect of disease-related immunosuppression nor a result of sequestration of *M. tuberculosis*-specific T cells at sites of active disease. Rather, the decline in ESAT-6-specific T cells with therapy, which reduces bacterial load by several orders of magnitude, suggests that, within a given individual, the frequency of ESAT-6-specific T cells is related to antigen load. This observation was made possible by using an assay that directly quantitates antigen-specific T cells without involving in vitro proliferation. Our finding is somewhat analogous to the decay in virus-specific CD8 and CD4 T cell frequencies, directly enumerated from peripheral blood, in HIV-infected patients during combination antiretroviral therapy and, in general for intracellular pathogens, frequencies of antigen-specific T cells, when directly quantitated ex vivo, appear to be driven by antigen load.

Although there is no quantitative absolute measure of bacterial or antigen load in tuberculosis, they must be directly and closely inter-related. Antigen load is almost certainly much lower in HHCs than in patients and, amongst patients, will obviously be lower in TBLN patients and C−PTB patients than in C+PTB patients. Given that antigen load appears to drive ESAT-6-specific CD4 T cell frequencies, it is remarkable that the *M. tuberculosis*-infected subjects with lower antigen loads have higher levels of ESAT-6-specific CD4 T cells. This inverse correlation is similar to that observed for virus-specific CD8 T cell frequencies and plasma viral load in HIV-infected patients, a finding which provided important support for the protective role for CD8 T cells in control of HIV and which depended crucially upon a means to quantify antigen-specific T cells ex vivo directly from peripheral blood. Thus, consideration of the frequencies of ESAT-6-specific T cells in the context of the differing bacterial load in the different groups of *M. tuberculosis*-infected subjects, lends further support to our hypothesis that these T cells mediate containment of *M. tuberculosis* in vivo. All groups of patients had similar proportions of individuals who had undergone treatment except for the HHCs, none of whom had received chemoprophylaxis. Moreover, the effect of treatment on ESAT-6 peptide-specific T cell frequencies appears to be similar for all groups of patients followed up (FIG. 2). Thus, the differences in ESAT-6-specific CD4 T cell frequencies between the 3 groups of patients are unlikely to result from differences in duration of treatment, although this may not apply to the HHCs.

Our interpretation of these findings is that, at the time of initial infection with *M. tuberculosis*, HHCs mount a strong, high frequency Th1-type CD4 T cell response to *M. tuberculosis* and, in particular, to ESAT-6, and so limit bacterial replication. Individuals who go on to develop active disease, by contrast, make a weak CD4 T cell response and the bacteria are allowed to reach a higher equilibrium bacterial load resulting in disease. Thus, HHCs maintain a high frequency of ESAT-6-specific CD4 T cells with limited antigenic stimulation from a low bacterial load, while in C+PTB patients, a high bacterial load stimulates weaker, less efficient proliferation of antigen-specific CD4 T cells in vivo. This model is analogous to that proposed for certain chronic viral infections, where virus-specific CD8 T cells are believed to mediate protective immunity. The difference between HHCs and PTB patients may lie in an individual's T cell responsiveness, which has previously been defined as the rate at which pathogen-specific T cells proliferate in vivo after encountering an infected host cell. Indeed, the early emergence and efficient proliferation of IFN-γ-secreting CD4 T cells in vivo has recently been identified as a crucial factor in the early containment of mycobacterial infection in murine models. ESAT-6 contains multiple CD4 T cell epitopes. FIG. 3 shows that several ESAT-6-derived peptides are widely recognized by T cells from an ethnically and genetically diverse range of patients and HHCs, suggesting that these peptides may be permissively restricted by a wide range of HLA class II haplotypes. The hierarchy of immunodominance using the ex vivo ELISPOT assay (FIG. 3) is quite different to that reported by others using more conventional assays that depend on in vitro proliferation. In particular, the striking immunodominance of peptides ESAT-6$_{1-15}$ and ESAT-6$_{71-85}$ has not been previously recognized to the extent observed here, and might reflect the fact that the ex vivo ELISPOT assay can detect T cells that have lost their in vitro proliferative potential. We therefore tested these, and the other ESAT-6-derived peptides, for their ability to stimulate T cells in lymphoproliferation assays. Although for most peptides there was a broad concordance between T cell responses in these assays and in the ex vivo ELISPOT, for peptides ESAT-6$_{1-15}$ and ESAT-6$_{71-85}$ there was a marked discrepancy (Table 2). The impaired ability of ESAT-6$_{1-15}$ specific and ESAT-6$_{71-85}$-specific T cells to proliferate in vitro probably explains why the immunodominance of these peptides was not hitherto fully appreciated. Interestingly, however, these T cells did proliferate in vitro if stimulated with IL-2 as well as peptide.

Since peptides ESAT-6$_{1-15}$ and ESAT-6$_{71-85}$ are recognised ox vivo by T cells from a very high proportion of *M. tuberculosis*-infected subjects, their HLA restriction is of special interest. Immunodominant, permissively restricted CD4 epitopes are usually HLA-DR-restricted and this is the case in tuberculosis. Surprisingly, peptides ESAT-6$_{1-15}$ and ESAT-6$_{71-85}$ were shown to be HLA-DQ-restricted in ELISPOT assays (FIG. 4). These are, to our knowledge, the first immunodominant HLA-DQ-restricted mycobacterial epitopes to be identified.

Having found that most *M. tuberculosis*-infected individuals have high frequencies of ESAT-6-specific IFN-γ- secreting CD4 T cells, we asked whether ESAT-6-specific Th2-type CD4 T cells are also induced to a similar extent. Ex vivo ELISPOT assays for IL-4 in a subset of patients and HHCs showed that, in contrast to the almost universal presence of ESAT-6-specific IFN-γ-secreting T cells in *M. tuberculosis*-infected subjects. IL-4-secreting T cells specific for ESAT-6 are rare. ESAT-6-specific CD4 T cells induced by natural *M. tuberculosis* infection thus have a highly Th1-polarised pattern of cytokine secretion.

We have identified a population of circulating IFN-γ-secreting *M. tuberculosis* antigen-specific CD4 T cells that circulate at high frequencies in asymptomatic individuals with latent *M. tuberculosis* infection, as well as tuberculosis patients. Our direct quantitative ex vivo approach led to certain key findings that have not been recognized using previous assays. Unlike other cellular immune responses in tuberculosis, frequencies of ESAT-6-specific CD4 T cells decay progressively with treatment, suggesting that these T cell frequencies are driven, at least in part, by antigen load. Therefore, patients with more extensive disease and higher bacterial loads would be expected to have the highest antigen-specific T cell frequencies. However, we observed the opposite: between groups of tuberculosis patients, the frequencies of these T cells appear to correlate with clinically-defined protective immunity; that is they correlate inversely with inferred bacterial load. These findings are consistent with a role for this population of Th1-type antigen-specific CD4 T cells in the containment of *M. tuberculosis* in vivo. These results, together with the fact that ESAT-6 contains multiple CD8 T cell epitopes, suggest that this antigen may be a target of protective immune responses in *M. tuberculosis*-infected humans; its absence from *M. bovis* BCG might thus account, in part, for the limited efficacy of BCG vaccination.

EXAMPLE 5

The Detection of CD4 T Cells in Individuals with Latent Infection

Methods

Study Population

All subjects were recruited prospectively in Mumbai and Oxford. A heparinized blood sample was drawn after obtaining informed consent.

50 patients with clinical and radiographic features consistent with tuberculosis and with positive cultures for *M. tuberculosis* from one or more clinical specimens, were recruited. 45 patients had pulmonary tuberculosis, 4 had tuberculous lymphadenitis and one had tuberculous pleuritis. 6 patients (5 pulmonary and one pleural tuberculosis) were HIV antibody positive. None of the other 44 patients had clinical features suggestive of HIV infection. The mean age of the patients was 33 years (range: 14–69) and the male:female ratio was 33:17. The patients were ethnically diverse comprising Maharashtrans (n=28), Gujaratis (n=6), Muslims (n=6), South Indians (n=4), Punjabis (n=3), Uttar Pradeshis (n=2) and Sindhis (n=1). 35 patients (70%) had received less than one mointh's therapy or were untreated at the time of venepuncture for ELISPOT assays; the remaining 15 patients were at later time points in their treatment course (<1 year).

108 healthy residents of Mumbai were prospectively recruited at an executive health check-up clinic; all were corporate executives requested to attend by their employers for insurance medicals and none had self-referred with symptoms. 7 subjects gave a past medical history of tuberculosis and one was resident in Zambia: these 8 subjects were excluded. The remaining 100 subjects all had normal chest radiography and none had any features of HIV infection. The male:female ratio was 78:22 and the mean are was 47 years (range: 18–70). The executives were ethnically diverse comprising Gujaratis (n=36), Maharashtrans (n=22), South Indians (n=14), Sindhis (n=7), Parsis (n=6), Punjabis (n=6), Marwaris (n=4), Muslims (n=3) and Bengalis (n=2).

40 healthy adult UK residents were recruited in Oxford. None had lived in a tuberculosis endemic country for more than one month and none had a past medical history of tuberculosis nor any known tuberculosis contact. All were ethnically white Caucasians, the male:female ratio was 21:19 and the mean age was 32 years (range: 23–49). 33/40 (32%) had a BCG scar or history of BCG vaccination.

Five bacteriologically confirmed tuberculosis patients were followed-up in the UK and ESAT-6 peptide-specific IFN-γ-secreting T cells were enumerated at different time points during anti-tuberculosis chemotherapy. Three of these patients had pulmonary tuberculosis, one had pleural disease (DD1) and one had tuberculous lymphadenitis (DD8).

ESAT-6 and CFP10-derived Peptides 17 peptides spanning the length of the ESAT-6 molecule and 18 peptides spanning the length of the CFP10 molecule were obtained and their identity tested as described for the peptides of Example 1. Each peptide was 15 amino acids long and overlapped its adjacent peptide by 10 residues. Sequence homology searches of the SwissProt and translated GenBank databases of all known protein sequences confirmed that the sequences of these peptides are uniquely restricted to the ESAT-6 and CFP10 proteins of *M. tuberculosis* complex. A response to one or more of these 35 peptides was scored as indicative of *M. tuberculosis* infection.

Ex vivo Enzyme-linked Immunospot (ELISPOT) Assay for Single Cell IFN-γ Release: Enumeration of Circulating ESAT-6 peptide-specific T cells from Peripheral Blood PBMC were separated from 15 mls blood by standard means and suspended in RPMI supplemented with L-glutamine 2 mM, penicillin 100 iu/ml and 10% heat-inactivated foetal calf serum (Sigma, St. Louis, Mo., USA) (R10). The ELISPOT assay was carried out as described in Example 1.

$2.5 \times 10^5$ PBMC ($3 \times 10^5$ for the UK subjects) were added in 100 μl R10/well and each of the 35 ESAT-6 and CFP10-derived peptides was added individually to single wells at 10 μg/ml. PPD (Batch RT49, Staatens Seruminstitut, Copenhagen, Denmark) was also tested at 20 μg/ml in duplicate wells. Phytohaemagglutinin (ICN Biomedicals, Aurora, Ohio, USA) at 5 μg/ml was added to duplicate positive control wells and no peptide to duplicate negative control wells. Whole recombinant ESAT-6 was added at 10 μg/ml for 11 tuberculosis patients and all healthy adults.

Incubation and further washes were performed as in Example 1. Responses were scored as positive if test wells contained at least 5 IFN-γ SFCs more than negative control wells and this number was at least twice that in negative control wells. Although the person performing the assays was not blind to the patients' tuberculosis status, the read-out in SFCs is quantitative, criteria for a positive response were stringent and pre-defined and SFCs in negative control wells were always below 15, so that positive responses were clear-cut. Positive and negative responses were immediately recoanizable by direct inspection of the plate, prior to precise enumeration with a magnifying lens. ELISPOT assay wells where the number of IFN-γ SFCs exceeds 250 cannot be precisely enumerated because the spots coalesce with each other. 250 SFCs per well (equivalent to 1000 SFCs per million PBMC) was therefore taken as the upper limit for accurate quantitation. The total number of ESAT-6- and CFP10-specific T cells in a given individual was calculated by summating all the IFN-γ SFCs specific for each of the different ESAT-6- or CFP 10-derived peptides (after subtraction of the background number of SFCs in the negative control wells), respectively, in that individual.

HIV Antibody Testing

HIV antibodies were detected by a rapid test with recombinant protein (Immunocomb II, Orgenics Ltd, Israel) followed by 2 different microtitre ELISA tests with synthetic peptides from different antigens (Laboratory Systems; Finland and Innogenetics, Innogenetics N.V, Belgium).

Tuberculin Skin Testing

1 TU of PPD (1:10,000) (Span Diagnostics, India) was injected intradermally in the flexor surface of the forearm to raise a pale white bleb. Cutaneous induration was measured with a ruler at 72 hrs and induration >10 mm was taken as positive.

Results

Figure 5:
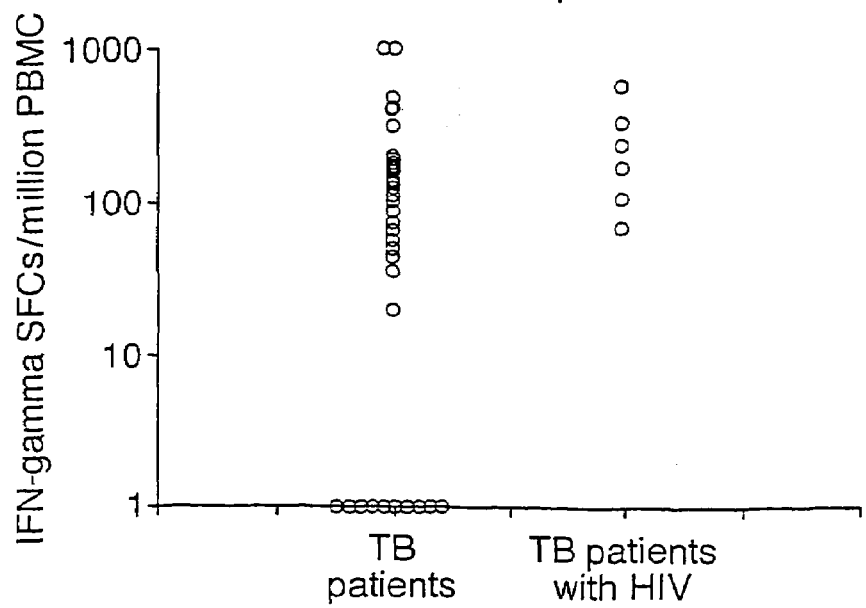
FIG. 5 shows frequencies of ESAT-6 peptide-specific and PPD-specific IFN-γ-secreting T cells enumerated by ex vivo enzyme-linked immunospot (ELISPOT) assay in 50 culture-confirmed tuberculosis patients in India. For each individual, the number of peptide-specific T cells for each of the ESAT-6-derived peptides was summated.

A high proportion of Indian tuberculosis patients have circulating ESAT-6 peptide-specific IFN-γ-secreting T cells and the ESAT-6-based ex vivo ELISPOT also detects tuberculosis patients with HIV infection. FIG. 5 shows that 40/50 bacteriologically confirmed cases of tuberculosis responded in the ESAT-6-based ex vivo ELISPOT assay. All 6 tuberculosis patients with HIV co-infection responded. The median number of ESAT-6 peptide specific T cells in the 40 patients who responded was 128 (inter-quartile range: 73–208) per million PBMC. Many patients responded to multiple peptides. Positive responses were clear-cut when compared with negative control wells and, out of a total of 40 positive responses, only 2 tuberculosis patients gave borderline positive responses (20 peptide-specific T cells per million PBMC). Of the 11 patients tested against whole recombinant ESAT-6, including 4 patients with HIV coinfection, all responded to recombinant antigen as well as to one or more ESAT-6-derived peptides. 6 tuberculosis patients (including 3 with HIV infection) underwent TST: all 6 were negative by Mantoux but positive in the ESAT-6-based ex vivo ELISPOT assay.

Figure 6A:
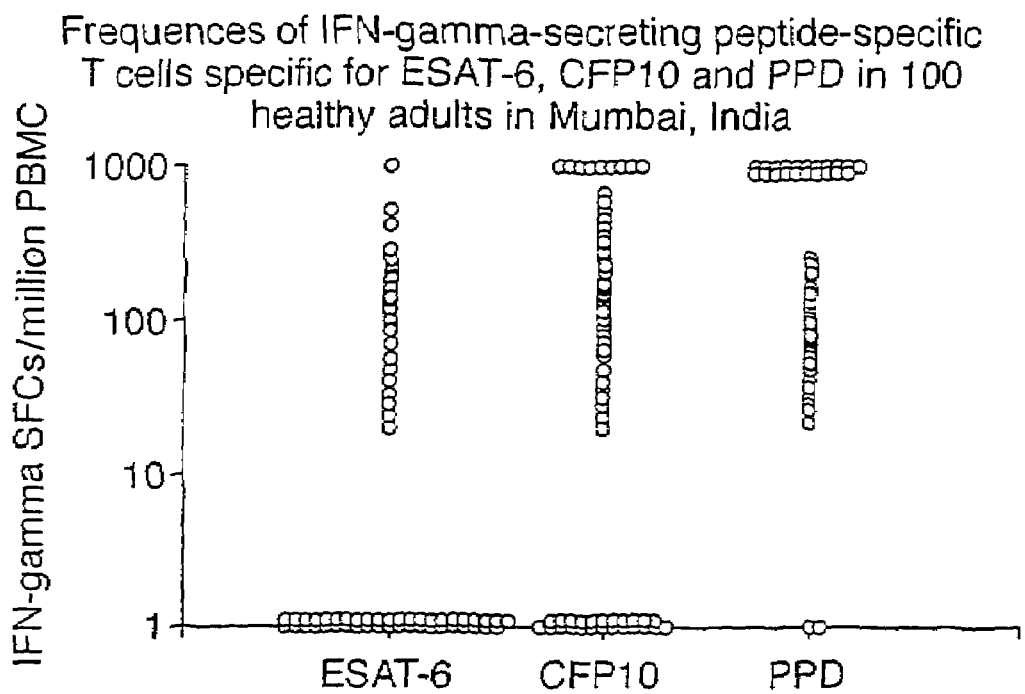
FIG. 6 shows frequencies of ESAT-6 and CFP10 peptide-specific, and PPD-specific IFN-γ-secreting T cells enumerated by ex vivo enzyme-linked immunospot (ELISPOT) assay in 100 healthy adults (with no past history of tuberculosis and normal chest radiography) resident in Mumbai, India (A) and 40 healthy adults resident in the UK (B). For each individual, the number of peptide-specific T cells for each of the ESAT-6- or CFP10-derived peptides was summated.

High Frequencies of RD1-encoded Antigen-specific IFN-γ-Secreting T Cells in 80% of Healthy Indian Adults 100 healthy adults with normal chest radiography and no history of tuberculosis were tested by ESAT-6 and CFP10 peptide-based ex vivo ELISPOT assay for IFN-γ. 56 had ESAT-6 peptide-specific T cells and 76 had CFP10 peptide-specific T cells detectable in peripheral blood (FIG. 6A). Overall, 80% responded to either ESAT-6 or CFP10 (Table 1). For the responders, the median frequency of ESAT-6 peptide-specific T cells was 86 (interquartile range: 43–156) per million PBMC and the median frequency of CFP10 peptide-specific T cells was 158 (interquartile range: 84-261) per million PBMC. These antigen-specific T cell frequencies are as high as (in the case of ESAT-6) or even higher (in the case of CFP10) than the frequency of PPD-specific IFN-γ-secreting T cells among the 98 individuals who responded to PPD: median=86 (interquartile range: 56–222) per million PBMC. CFP10 peptide-specific T cell frequencies were especially high and 9 individuals had over 1000 CFP10-specific IFN-γ-secreting T cells per million PBMC. The combined frequency of IFN-γ-secreting T cells specific for ESAT-6 and CFP10 derived peptides in the 80 individuals who responded to either of these 2 antigens (median=208 per million PBMC [interquartile range: 116–357]) is higher than the frequency of IFN-γ-secreting PPD-specific T cells. Thus, in healthy residents of a tuberculosis endemic area, these two antigens alone are a more potent target of IFN-γ-secreting T cells ex vivo than is PPD, which contains over 200 antigens.

Of the 56 healthy individuals who responded to ESAT-6-derived peptides, the majority (n=47) also responded to whole recombinant antigen, suggesting that processing and presentation of recombinant antigen occurs when it is added exogenously to PBMC in ELISPOT assays. This is consistent with our previous observations and supports the fact that the peptide-specific responses are not artifactual. We have previously observed that *M. tuberculosis*-infected individuals who respond to ESAT-6-derived peptides but not whole antigen in the ex vivo ELISPOT assay, have ESAT-6-specific CD8 T cells; the lack of recognition of whole antigen is because exogenously added ESAT-6 is not be processed through the MHC class I antigen processing pathway, whereas vaccinia virus recombinant for ESAT-6 will present to CD8 T cells. Thus, in the 9 individuals in whom peptide-specific responses were not accompanied by a response to exogenously added antigen, the T cell response to ESAT-6 was probably CD8-mediated.

Figure 6B:
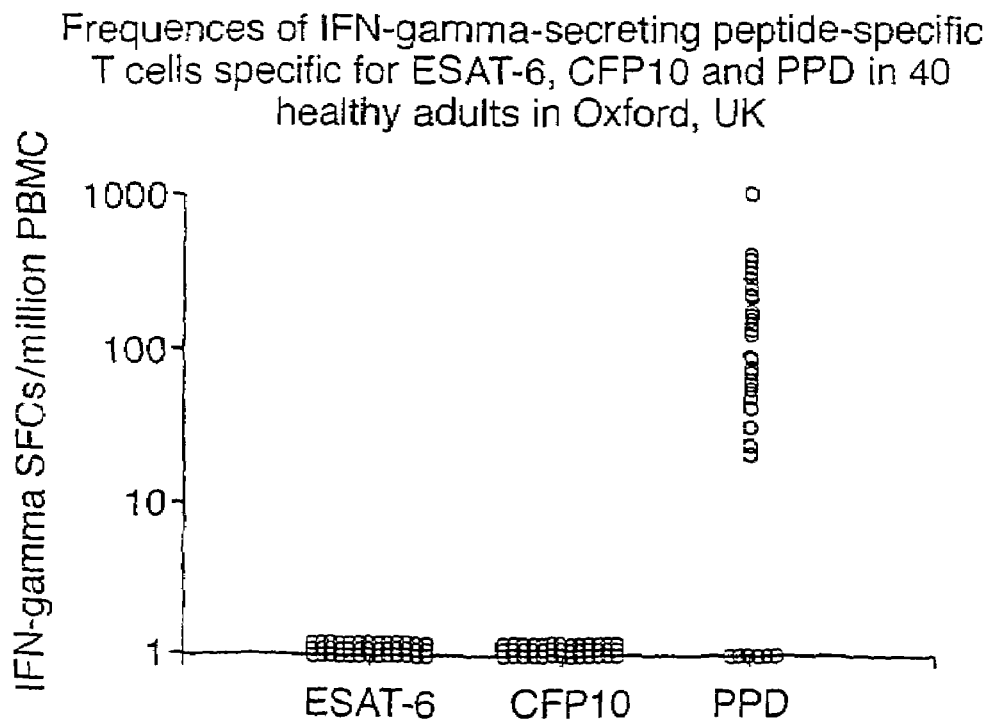

Absence of ESAT-6 and CFP10-specific T cells in Healthy Residents of a Non-Endemic Area 40 healthy adult UK residents with no past history of tuberculosis were tested prospectively by ESAT-6 and CFP10 peptide-based ex vivo ELISPOT assay for IFN-γ. None of the donors reported any tuberculosis contact. FIG. 6B shows that no donors responded to any of the CFP10 or ESAT-6 peptides. By contrast, 33/40 subjects responded to PPD in the ex vivo ELISPOT assay for IFN-γ with a median frequency of 83 (interquartile range: 53–215) PPD-specific T cells per million PBMC which was very similar to the frequency of PPD-specific T cells seen in the healthy Indian adults. The high prevalence of PPD-specific responses in the unexposed UK residents probably reflects the fact that 33/40 were BCG-vaccinated.

Figure 7A:
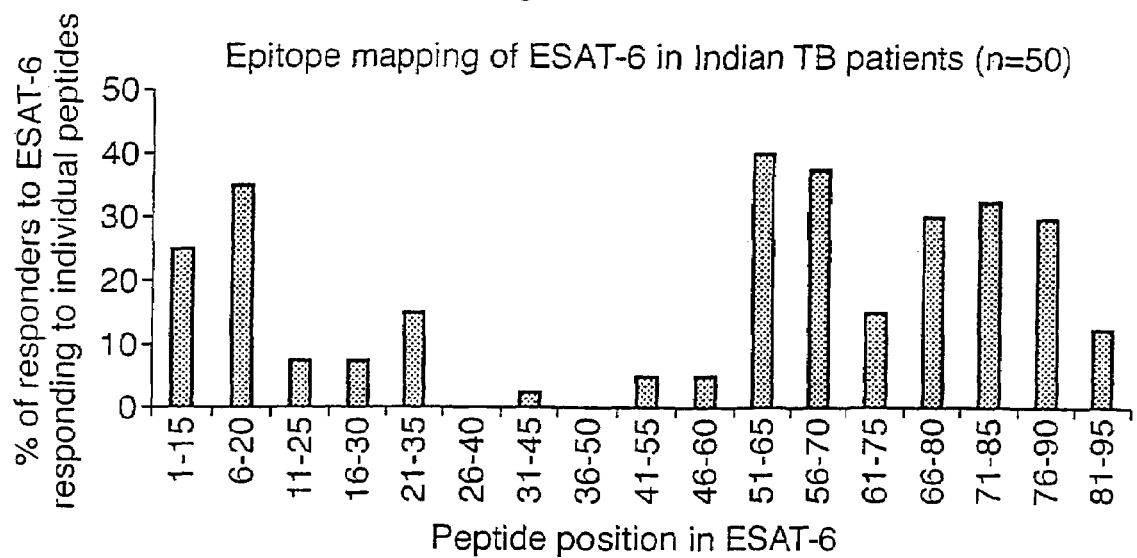
FIG. 7 shows epitope maps of ESAT-6 and CFP10. Epitope map of ESAT-6 in tuberculosis patients in India (A), epitope map of ESAT-6 in healthy Indian adults resident in Mumbai (B) and epitope map of CFP10 in healthy Indian adults resident in Mumbai (C). For each antigen the number of individuals responding to a given peptide is expressed as a percentage of the total number of subjects responding to that antigen.
Figure 7B:
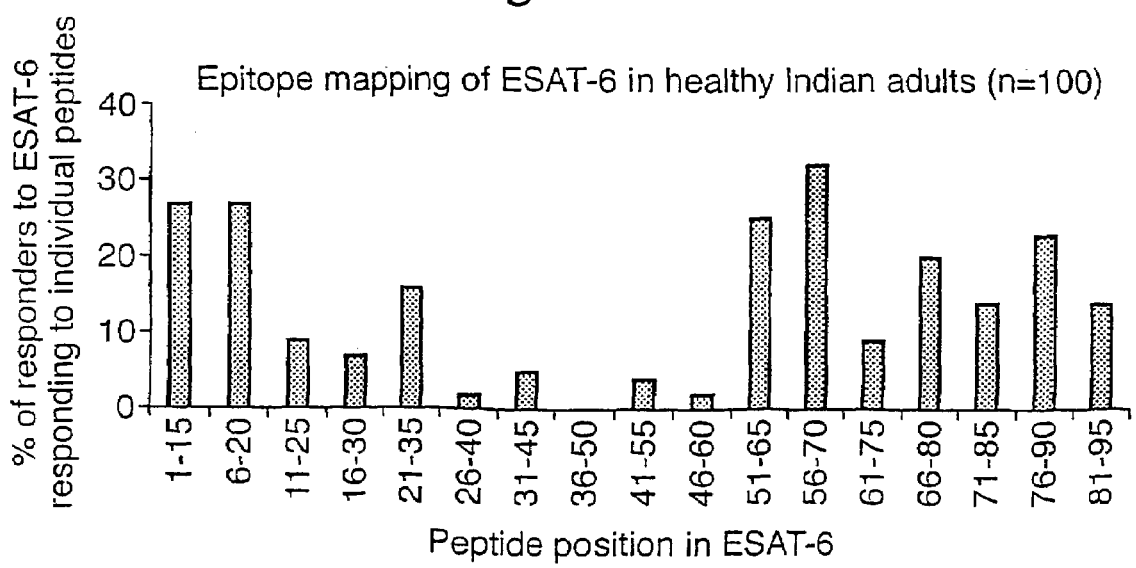

Epitope Mapping of ESAT-6 and CFP10 in Indian tuberculosis Patients and Healthy Adults Many Indian patients and healthy adults responded to multiple peptides and, as illustrated in FIGS. 7A & 7B, ESAT-6 contains multiple T cell epitopes which are concentrated at the amino and carboxy termini of the molecule. These highly immunogenic peptides are mostly CD4 T cell epitopes because T cell lines have been generated in vitro against peptides $ESAT-6_{1-15}$, $ESAT-6_{6-20}$, $ESAT-6_{16-30}$, $ESAT-6_{21-35}$, $ESAT-6_{31-45}$, $ESAT-6_{46-60}$, $ESAT-6_{51-65}$, $ESAT-6_{56-70}$, $ESAT-6_{66-80}$, $ESAT-6_{71-85}$, $ESAT-6_{76-90}$ and $ESAT-6_{81-95}$, and, in each case, peptide-specific responses were abrogated by immunomagnetic depletion of CD4 T cells (data not shown). We have previously identified 8-mer and 9-mer HLA class I-restricted CD8 epitopes in peptides 4 and 14 but, since these are strictly restricted by HLA-A6802 and HLA-B52 respectively, only a small proportion of infected people respond. In contrast to these CD8 epitopes, many of the CD4 epitopes were recognized by T cells from a relatively large percentage of the 150 ethnically diverse Indians in this study. For several of these peptides ($ESAT-6_{1-15}$, $ESAT-6_{6-20}$, $ESAT-6_{51-65}$ and $ESAT-6_{71-85}$), we have previously used anti-HLA-DR, -DQ and -DP monoclonal antibodies to block presentation to CD4 T cells in ELISPOT assays. In all tuberculosis patients and contacts where this was tested (n=14), the responses were MHC class 1-restricted. The pattern of ESAT-6 epitopes to which the tuberculosis patients responded is similar to that for the healthy subjects (FIGS. 7A & 7B).

Figure 7C:
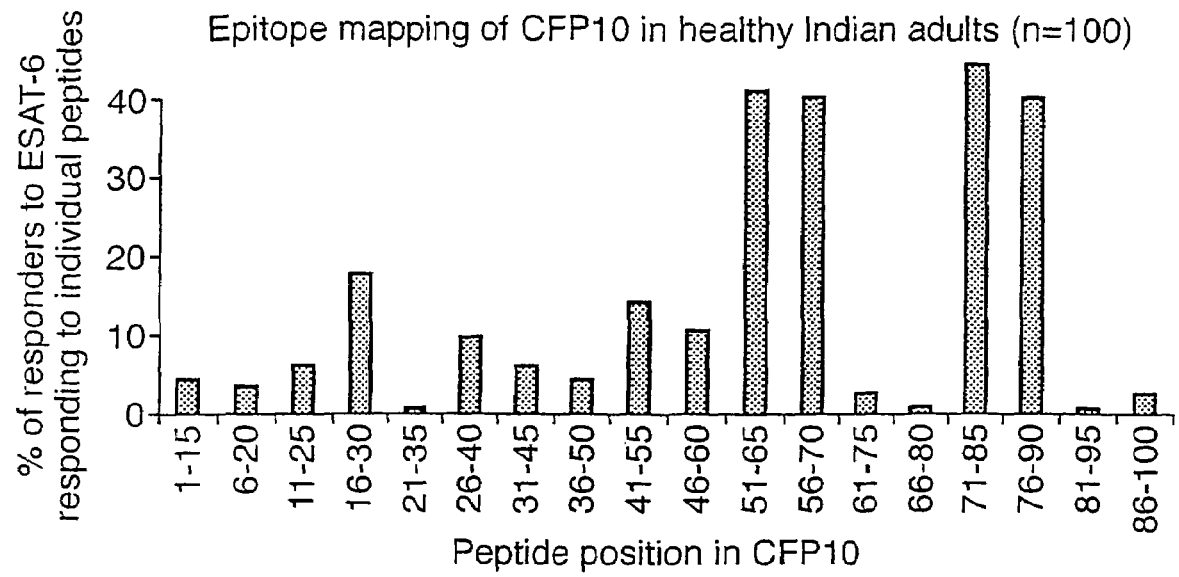

Analysis of the T cell response to the 18 overlapping CFP10 peptides in the hundred residents of Mumbai has generated the first epitope map of CFP10 (FIG. 7C). This reveals two strikingly immunodominant domains, $CFP_{51-70}$ and $CFP_{71-90}$; almost 50% of healthy Indians responded to peptides from these two regions. 15–20% of Indians responded to $CFP_{16-30}$ and $CFP_{41-60}$, identifying these peptides as additional immunogenic regions.

Figure 8:
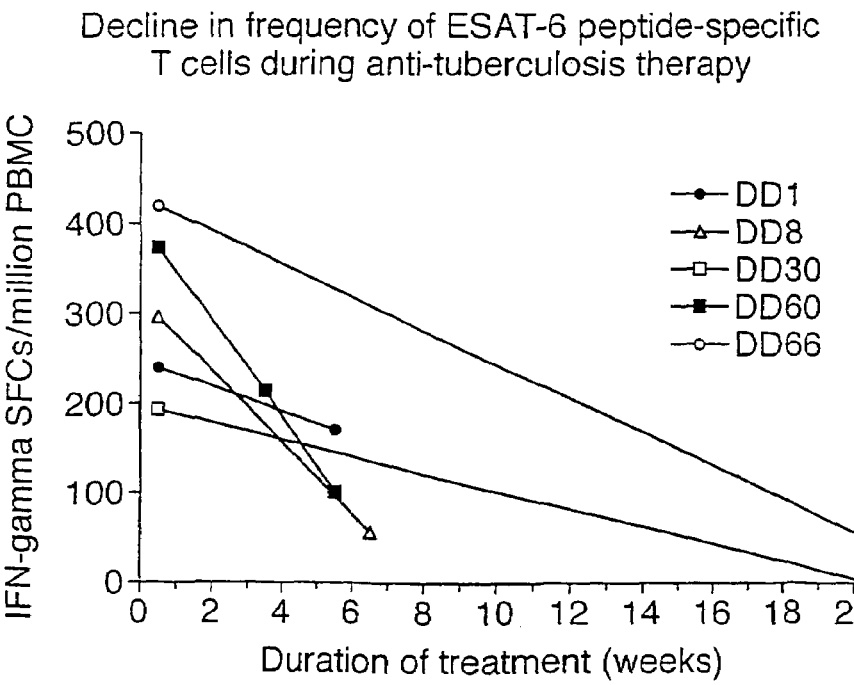
FIG. 8 shows the progressive decline in frequency of ESAT-6 peptide-specific IFN-γ-secreting T cells during anti-tuberculosis chemotherapy in a series of 5 culture-confirmed tuberculosis patients followed-up longitudinally. For each individual, the number of peptide-specific T cells for each of the ESAT-6-derived peptides, enumerated by the ex vivo enzyme-linked immunospot (ELISPOT) assay, was summated at each time point.

Progressive Decline in Frequency of ESAT-6 Peptide=specific IFN-γ-secreting T cells During Anti-Tuberculosis Treatment FIG. 8 shows the progressive fall in the frequency of ESAT-6 peptide-specific IFN-γ-secreting T cells during anti-tuberculosis treatment in a series of culture-confirmed tuberculosis cases followed up longitudinally in the UK (n=5). All patients had drug-sensitive isolates of M. tuberculosis and responded well to therapy.

Discussion

We have identified ESAT-6-specific IFN-γ-secreting T cells as an accurate marker of M. tuberculosis infection in patients with bacteriologically confirmed active disease and latently infected TST positive healthy household contacts of sputum smear positive tuberculosis cases. CFP10 shares the same species specificity as ESAT-6 and is thus absent from all strains of M. bovis BCG and the vast majority of environmental mycobacteria. Here we demonstrate that 80% of our sample of healthy Indian adults harbour circulating IFN-γ-secreting T cells specific for at least one of these two RD1 encoded antigens, ESAT-6- and CFP10. This suggests that at least 80% of residents of Mumbai have been exposed to, or are infected with, M. tuberculosis. The striking absence of ESAT-6 and CFP10-specific T cells in all the unexposed UK residents supports this conclusion and the fact that 33/40 of these subjects were BCG-vaccinated indicates moreover that this approach is highly specific and not confounded by BCG-vaccination. Given that all the Mumbai residents were asymptomatic and had normal chest radiography, M. tuberculosis infection in these individuals would, by definition, be latent rather than active.

Might the high prevalence of ESAT-6- and CFP10-specific T cells in this population result from exposure to a cross-reactive environmental antigen unrelated to M. tuberculosis that is present in India but absent in the UK? We consider this unlikely since sequence homology searches of the SwissProt and translated GenBank databases with each of the ESAT-6 and CFP10-derived peptides indicate that the sequences of all these peptides are uniquely restricted to ESAT-6 and CFP10 of M. tuberculosis complex. However, The esat-6 gene (and therefore very likely the gene for CFP10, which is within the same operon as esat-6) are present in 4 a typical mycobacteria: M. kansasii, szulgai, flavescens and marinum. It is thus conceivable that the ESAT-6 and CFP10-specific responses could result from infection with one of these organisms. To account for the striking dichotomy of ESAT-6- and CFP10-specific responses between India and the UK, an environmental mycobacterium would have to cause widespread infection in Mumbai but be absent in southern England. However, none of these mycobacteria fit this geographic distribution, nor are they specifically associated with tropical climates. Rather, M. kansasii is the most common non-HIV associated nontuberculous mycobacterium isolated from patients in southern England and is a recognized isolate from tap water in cities in this region. In contrast, M. kansasii disease has not been reported from Mumbai, although this may reflect under-reporting by local laboratories. The absence of RD1-encoded antigen-specific T cells in the 40 UK residents thus makes M. kansasii exposure an unlikely cause for the difference in responses between the UK and India. M. marinum infection is usually acquired by trauma in a salt-water or freshwater setting or whilst handling fish; these scenarios would be rare among the corporate executives attending for insurance medicals at our institution in Mumbai. M. szulgai and M. flavescens are very rare causes of infection in humans. M. szulgai has been isolated from patients throughout the world, including the UK, but environmental isolates have not been reported. M. flavescens has been found in water supplies in several European countries and thus, as with M. kansasii, cannot account for the widespread sensitization to ESAT-6 and CFP10 in Mumbai residents and the striking absence of sensitization in the UK donors.

The circulating IFN-γ-secreting T cells specific for ESAT-6 and CFP10 were capable of rapid effector function since they released IFN-γ in the ex vivo ELISPOT assay without requiring prior in vitro stimulation. This suggests that the donors are latently infected with tubercle bacilli that continue to secrete ESAT-6 and CFP10, since high frequencies of circulating effector T cells are probably maintained by recent encounter with antigen in vivo. Since ongoing, active secretion of ESAT-6 and CFP10 requires metabolically active and viable bacilli, the presence of circulating ESAT-6 and CFP10-specific effector T cells in healthy donors suggests that they are latently infected and not merely exposed at some point in the past. Nonetheless, we cannot rule out the possibility that circulating IFN-γ-secreting T cells undergo repeated in vivo stimulation as a result of long term persistence of ESAT-6 and CFP10 in dendritic cells in the absence of viable bacilli. However, longitudinal follow-up of tuberculosis patients in the UK shows that the frequency of ESAT-6 peptide-specific IFN-γ-secreting CD4 T cells declines progressively during the course of anti-tuberculosis chemotherapy (FIG. 8), suggesting that the frequencies of these T cells are maintained in vivo by ESAT-6 secreted by viable bacilli.

TST surveys in India have generated widely varying results, with the prevalence of TST positivity in adults ranging from 38–81%. This wide variation in part reflects poor standardisation of PPD preparations used, differences in methodology, inconsistency in reading of skin test results, misclassifications and the instability of delayed type hypersensitivity over time. These limitations, together with the intrinsic poor specificity of PPD, render estimates of the prevalence of latent M. tuberculosis infection by TST surveys doubtful. Our novel, quantitative approach has generated a more objective estimate that is not confounded by prior BCG vaccination and is unlikely to be affected by environmental mycobacterial infection. The 80% prevalence in corporate executives is higher than would have been expected on the basis of past TST surveys, especially considering that the latter have all been carried out in rural areas or urban slums. Interestingly, the prevalence of positive results by RD1 encoded antigen-based ELISPOT was higher in men (64/78 =82%) than in women (16/22 =73%) which parallels the difference between the sexes seen in TST surveys. This estimate of the prevalence of latent infection is thus unexpectedly high for both men and women, particularly if one takes into account the relative affluence and lack of domestic overcrowding in our population sample.

In contrast to the ELISPOT assay for IFN-γ incorporating the two RD1 encoded antigens, the use of PPD does not differentiate between the Mumbai-resident and UK-resident populations, with 98% and 85% of these populations, respectively, responding to PPD (FIGS. 6A & 6B). The 83% (33/40) prevalence of PPD-specific responses in the tuberculosis unexposed UK residents very likely results from 33/40 being BCG-10 vaccinated. Thus, unlike ESAT-6- and CFP10-specific T cells, PPD-specific IFN-γ-secreting T cells do not discriminate between latently infected residents of a tuberculosis endemic area and unexposed, BCG-vaccinated residents of a non-endemic region; this underscores the practical advantage of using defined antigens with a highly restricted species distribution.

Among the 50 patients with active tuberculosis who were tested with ESAT-6-derived peptides only, 80% had ESAT-6 peptide-specific T cells by ex vivo ELISPOT. It is not clear why this response rate is lower than that found among a group of patients with active tuberculosis recruited in the UK, where 45/47 (96%) patients responded to one or more ESAT-6-derived peptides, but the following 3 factors are likely to be relevant. First, peptide ESAT-$6_{1-15}$ was an immunodominant and permissively recognized epitope in the previous UK study, with 60% of patients responding to this peptide alone, whereas in Mumbai, only 25% of patients respond to this peptide (FIG. 7A). This probably reflects the different HLA backgrounds of the 2 populations. Although 50% of the UK tuberculosis patients were from the Indian Subcontinent, none were Maharashtrans and the remaining 50% were Afrocarribeans or whites. Of the tuberculosis patients recruited in India, 56% were Maharashtrans and the remainder from other Indian ethnic groups. Thus, peptide ESAT-$6_{1-15}$ might be restricted by HLA class II molecules that are rare among Maharashtrans. Second, the median frequency of total ESAT-6-specific T cells in the Mumbai patients who responded (128 per million PBMC; interquartile range: 72–208) was somewhat lower than in the London pulmonary tuberculosis patients (177 per million PBMC; interquartile range: 104–392). Mumbai patients would therefore be more likely to have very low numbers of circulating ESAT-6-specific T cells and if the absolute frequency of ESAT-6-specific T cells in a given patient were below the threshold of our assay (20 per million PBMC), such patients would not be detected by the ex vivo ELISPOT assay. Third, the two UK patients who did not respond had very advanced pulmonary tuberculosis with cachexia and, whereas this was rare in the UK patients, many of the Mumbai patients presented at an advanced stage of disease. Interestingly, all 6 of the tuberculosis patients with HIV infection had detectable ESAT-6 peptide-specific T cells by ex vivo ELISPOT. This preliminary result is the first demonstration of ESAT-6-specific T cells in HIV-infected tuberculosis patients and suggests that the clinical and epidemiologic utility of the ex vivo ELISPOT assay for *M. tuberculosis* antigen-specific T cells may be maintained even in HIV-infected individuals.

Finally, the frequency of ESAT-6 and CFP10-specific T cells among healthy urban Indians, as well as the prevalence of positive responses, was also very high (Table 3). The median frequency of total CFP10 peptide-specific T cells for the CFP10 responders (158 per million PBMC; interquartile range: 84–261) was actually higher than the median frequency of PPD-specific T cells for the PPD responders (86 per million PBMC; interquartile range: 56–222), while the median frequency of total ESAT-6 peptide-specific T cells (86 per million PBMC; interquartile range: 43–156) was similar to that for PPD. Many of these responses were moreover directed against discrete immunodominant regions within the ESAT-6 and CFP10 molecules (FIGS. 7A & 7B). Immune responses in patients with active tuberculosis probably contribute to pathogenesis and tissue destruction, as well as protection. This intense and highly focused T cell response in residents of a tuberculosis endemic region who are free of active tuberculosis indicates that these RD1-encoded antigen-specific T cells are not necessarily associated with active disease per se. Rather, the presence of these T cells in latently infected healthy subjects is consistent with a protective role in the long-term control of *M. tuberculosis* in vivo.

In conclusion, we have demonstrated that 80/100 healthy adults in Mumbai have high frequencies of T cells specific for two RD1 encoded *M. tuberculosis* antigens, suggesting that at least 80% of this urban population may be latently infected with *M. tuberculosis*. This represents the first estimate of the prevalence of latent *M. tuberculosis* infection in an endemic region using a T cell-based approach with antigens of tightly defined species specificity.

REFERENCES

1. Lalvani, A., R. Brookes, S. Hambleton, W. J. Britton, A. V. Hill, and A. J. McMichael. 1997. Rapid effector function in CD8+ memory T cells. *J. Exp Med.* 186:859–65.
2. Lalvani, A., R. Brookes, R. J. Wilkinson, A. S. Malin, A. A. Pathan, P. Andersen, H. Dockrell, G. Pasvol, and A. V. Hill. 1998. Human cytolytic and interferon gamma-secreting CD8+ T lymphocytes specific for *Mycobacterium tuberculosis*. *Proc Natl Acad Sci* USA. 95:270–5.
3. Pathan, A. A., K. A. Wilkinson, R. J. Wilkinson, M. Latif, H. McShane, G. Pasvol, A. V. Hill, and A. Lalvani. 2000. High frequencies of circulating IFN-gamma-secreting CD8 cytotoxic T cells specific for a novel MHC class I-restricted *Mycobacterium tuberculosis* epitope in *M. tuberculosis*-infected subjects without disease. *Eur J Immunol.* 30:2713–21.

TABLE 1

Demogranhic characteristics and median frequencies of ESAT-6 peptide-specific IFN-γ SFCs/million PBMC for all participants.

|  | UC (n = 32) | HHC (n = 27) | TBLN (n = 11) | C-PTB (n = 8) | C+PTB (n = 25) |
|---|---|---|---|---|---|
| Mean age in years | 32 | 37 | 32 | 31 | 34 |
| (range) | (22–65) | (19–65) | (27–41) | (19–54) | (19–61) |
| Sex | 15 M/17 F | 16 M/11 F | 5 M/6 F | 8 M/0 F | 17 M/8 F |
| Ethnicity: |  |  |  |  |  |
| ISC | 10 | 16 | 7 | 6 | 12 |
| African | 0 | 4 | 4 | 1 | 5 |

TABLE 1-continued

Demographic characteristics and median frequencies of ESAT-6 peptide-specific IFN-γ SFCs/million PBMC for all participants.

|  | UC (n = 32) | HHC (n = 27) | TBLN (n = 11) | C−PTB (n = 8) | C+PTB (n = 25) |
|---|---|---|---|---|---|
| White | 22 | 5 | 0 | 1 | 7 |
| Oriental | 0 | 2 | 0 | 0 | 1 |
| No. of subjects responding to ESAT-6 peptides (%) | 0 (0) | 23 (85) | 10 (91) | 7 (88) | 23 (92) |
| Median no. ESAT-6-specific IFN-γ SFCs/ million PBMC (IQ range)* | 0 (0–0) | 667 (197–965) | 811 (570–1505) | 474 (272–1267) | 177 (104–392) |

*Median of the number of ESAT-6 peptide-specific CD4 T cells (summated for all the peptides) for all the responders within a group (C+ = culture positive; C− = culture negative; PTB = pulmonary tuberculosis; TBLN = tuberculous lymphadenitis; HHC = healthy household contact; UC = unexposed control; IQ range = inter-quartile range; ISC = Indian subcontinent).

TABLE 2

Most ESAT-6-derived peptides are targets of CD4 T cells: the number of donors for whom a peptide-specific T cell line was shown to be CD4 positive by immunomagnetic depletion is shown in proportion to the total number of donors in whom T cell lines were tested for that peptide.

| Peptide | Sequence | Peptide-specific T cell lines shown to be CD4 positive | Response in ex vivo ELISPOT (n = 15) | Response in lympho-proliferation assay (n = 15) |
|---|---|---|---|---|
| ESAT-6$_{1-15}$ | MTEQQWNFAGIEAAA | 10/10 | 12 | 1 |
| ESAT-6$_{6-20}$ | WNFAGIEAAASAIQG | 4/4 | NT | NT |
| ESAT-6$_{11-25}$ | IEAAASAIQGNVTSI | 1/1 | 3 | 1 |
| ESAT-6$_{16-30}$ | SAIQGNVTSIHSLLD | 3/4 | 4 | 0 |
| ESAT-6$_{21-35}$ | NVTSIHSLLDEGKQS | 4/4 | 4 | 1 |
| ESAT-6$_{26-40}$ | HSLLDEGZQSLTKLA | NT | 2 | 0 |
| ESAT-6$_{31-45}$ | EGKQSLTKLAAAWGG | 1/1 | 1 | 0 |
| ESAT-6$_{36-50}$ | LTKLAAAWGGSGSEA | 1/1 | 1 | 0 |
| ESAT-6$_{41-55}$ | AAWGGSGSEAYQGVQ | NT | 0 | 0 |
| ESAT-6$_{46-60}$ | SGSEAYQGVQQKWDA | 1/1 | 1 | 0 |
| ESAT-6$_{51-65}$ | YQGVQQKWDATATEL | 3/3 | 4 | 4 |
| ESAT-6$_{56-70}$ | QKWDATATELNNALQ | 2/3 | 3 | 2 |
| ESAT-6$_{61-75}$ | TATELNNALQNLART | 1/2 | 1 | 0 |
| ESAT-6$_{66-80}$ | NNALQNLARTISEAG | 8/9 | 8 | 7 |
| ESAT-6$_{71-85}$ | NLARTISEAGQAMAS | 8 | 11 | 5 |
| ESAT-6$_{76-90}$ | ISEAGQAMASTEGNV | 6 | 11 | 9 |
| ESAT-6$_{81-95}$ | QAMASTEGNVTGMFA | 2 | 0 | 0 |

T cells specific for certain immunodominant ESAT-6-derived peptides, as enumerated by ex vivo ELISPOT, were not detectable in lymphorproliferation assays: PBMC from 15 subjects were tested in parallel in ex vivo ELISPOT assays for IFN-γ and $^3$H-thymidine incorporation assays, in which a stimulation index of 3 or more was taken as positive.

TABLE 3

Summary of summated responses to ESAT-6- and CFP10-derived peptides and PPD by ex vivo enzyme-linked immunospot (ELISPOT) assay for IFN-γ in healthy adults resident in India and the UK. (Median frequencies of T cells refer to antigen-specific T cell frequencies in responders only.)

|  | Healthy adults: Mumbia, India | | | | Healthy adults: Oxford, UK | | | |
| --- | --- | --- | --- | --- | --- | --- | --- | --- |
| Antigen | ESAT-6 | CFP10 | ESAT-6 or CFP10 | PPD | ESAT-6 | CFP10 | ESAT-6 or CFP10 | PPD |
| No. tested by ex vivo ELISPOT | 100 | 100 | 100 | 100 | 40 | 40 | 40 | 40 |
| No. positive (%) | 56 (56) | 76 (76) | 80 (80) | 98 (98) | 0 (0) | 0 (0) | 0 (0) | 33 |
| Median frequency of antigen-specific IFN-γ-secreting T cells/ $10^6$ PBMC (interquartile range) | 86 (43–156) | 158 (84–261) | 208 (116–357) | 86 (56–222) | 0 | 0 | 0 | 83 (53–215) |

TABLE 4

```
ESAT-6:  M T E Q Q W N F A G I E A A A S A I Q G N V T S I H S L L D
         |   |           |       |                 |
CFP10:   M A E M K T D A A T L A Q E A G N F E R I S G D L K T Q I D

ESAT-6:  E G K Q S L T K L A A A W G G S G S E A Y Q G V Q Q K W D A
                   |     |       |   |                   |
CFP10:   Q V E S T A G S L Q G Q W R G A A G T A A Q A A V V R F Q E

ESAT-6:  T A T E L N N A L Q N L A R T I S E A G
             |               |         | |
CFP10:   A A N K Q K Q E L D E I S T N I R Q A G V Q Y S R A D E E Q

EAST-6:  - Q A M A S T - E G N V T G M F A    (SEQ ID NO:1)
           | |   |       |
CFP10:   Q Q A L S S Q - M G F *              (SEQ ID NO:2)
```

The invention claimed is:

1. Method of determining the efficacy of treatment for *M. tuberculosis* infection in an individual comprising determining in samples from the individual whether the level of T cells specific for an antigen of said *M. tuberculosis* has decreased after the treatment, wherein said antigen is ESAT-6 or CFP 10, thereby determining the efficacy of the treatment and wherein said determining is by quantification of said T cells as directly ex vivo cells.

2. Method according to claim 1 wherein the T cells are CD4 T cells.

3. Method according to claim 1 comprising detecting the level of the said T cells in a first sample taken before the treatment and in a second sample taken after the treatment.

4. Method according to claim 1 wherein the T cells detected are freshly-isolated T cells from peripheral blood.

5. Method according to claim 1 wherein the level of T cells snecific for said antigen is determined by contacting cells of the sample with said antigen.

6. Method according to claim 5 wherein said determining is performed by detection of a cytokine secreted by the T cells specific for said antigen.

7. Method according to claim 6 in which the cytokine is IFN-γ.

8. Method according to claim 6 in which the cytokine is detected by allowing the cytokine to bind to an immobilized antibody specific to the cytokine and then detecting the presence of the antibody/cytokine complex.

9. Method according to claim 1 comprising determining whether after the treatment a decreased level of T cells specific for said *M. tuberculosis* antigen continues to be detectable, which decreased level is indicative of latent infection.

10. Method according to claim 1 wherein the level of T cells specific for said antigen is determined by contacting cells of the sample with one or more peptides selected from fragments of said antigen which are capable of recognition by T cells of said individual.

11. Method according to claim 10 wherein said determining is performed by detection of a cytokine secreted by the T cells specific for said antigen.

12. Method according to claim 11 in which the cytokine is IFN-γ.

13. Method according to claim 11 in which the cytokine is detected by allowing the cytokine to bind to an immobilized antibody specific to the cytokine and then detecting the presence of the antibody/cytokine complex.

* * * * *

SEQUENCE LISTING

<160> NUMBER OF SEQ ID NOS: 19

<210> SEQ ID NO 1
<211> LENGTH: 95
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ser
1               5                   10                  15

Ala Ile Gln Gly Asn Val Thr Ser Ile His Ser Leu Leu Asp Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 2
<211> LENGTH: 100
<212> TYPE: PRT
<213> ORGANISM: Mycobacterium tuberculosis

<400> SEQUENCE: 2

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
            20                  25                  30

Glu Ser Thr Ala Gly Ser Leu Gln Gly Gln Trp Arg Gly Ala Ala Gly
        35                  40                  45

Thr Ala Ala Gln Ala Ala Val Val Arg Phe Gln Glu Ala Ala Asn Lys
    50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

<210> SEQ ID NO 3
<211> LENGTH: 15
<212> TYPE: PRT
<213> ORGANISM: Mycobacterium tuberculosis

<400> SEQUENCE: 3

Met Thr Glu Gln Gln Trp Asn Phe Ala Gly Ile Glu Ala Ala Ala
1               5                   10                  15

<210> SEQ ID NO 4
<211> LENGTH: 15
<212> TYPE: PRT
<213> ORGANISM: Mycobacterium tuberculosis

<400> SEQUENCE: 4

Trp Asn Phe Ala Gly Ile Glu Ala Ala Ala Ser Ala Ile Gln Gly
1               5                   10                  15

<210> SEQ ID NO 5
<211> LENGTH: 15
<212> TYPE: PRT
<213> ORGANISM: Mycobacterium tuberculosis

<400> SEQUENCE: 5

Ile Glu Ala Ala Ala Ser Ala Ile Gln Gly Asn Val Thr Ser Ile
1               5                   10                  15

<210> SEQ ID NO 6
<211> LENGTH: 15
<212> TYPE: PRT
<213> ORGANISM: Mycobacterium tuberculosis

<400> SEQUENCE: 6

Ser Ala Ile Gln Gly Asn Val Thr Ser Ile His Ser Leu Leu Asp
1               5                   10                  15

<210> SEQ ID NO 7
<211> LENGTH: 15
<212> TYPE: PRT
<213> ORGANISM: Mycobacterium tuberculosis

<400> SEQUENCE: 7

Asn Val Thr Ser Ile His Ser Leu Leu Asp Glu Gly Lys Gln Ser
1               5                   10                  15

<210> SEQ ID NO 8
<211> LENGTH: 15
<212> TYPE: PRT
<213> ORGANISM: Mycobacterium tuberculosis -continued

```
<400> SEQUENCE: 8

His Ser Leu Leu Asp Glu Gly Lys Gln Ser Leu Thr Lys Leu Ala
1               5                   10                  15

<210> SEQ ID NO 9
<211> LENGTH: 15
<212> TYPE: PRT
<213> ORGANISM: Mycobacterium tuberculosis

<400> SEQUENCE: 9

Glu Gly Lys Gln Ser Leu Thr Lys Leu Ala Ala Ala Trp Gly Gly
1               5                   10                  15

<210> SEQ ID NO 10
<211> LENGTH: 15
<212> TYPE: PRT
<213> ORGANISM: Mycobacterium tuberculosis

<400> SEQUENCE: 10

Leu Thr Lys Leu Ala Ala Ala Trp Gly Gly Ser Gly Ser Glu Ala
1               5                   10                  15

<210> SEQ ID NO 11
<211> LENGTH: 15
<212> TYPE: PRT
<213> ORGANISM: Mycobacterium tuberculosis

<400> SEQUENCE: 11

Ala Ala Trp Gly Gly Ser Gly Ser Glu Ala Tyr Gln Gly Val Gln
1               5                   10                  15

<210> SEQ ID NO 12
<211> LENGTH: 15
<212> TYPE: PRT
<213> ORGANISM: Mycobacterium tuberculosis

<400> SEQUENCE: 12

Ser Gly Ser Glu Ala Tyr Gln Gly Val Gln Gln Lys Trp Asp Ala
1               5                   10                  15

<210> SEQ ID NO 13
<211> LENGTH: 15
<212> TYPE: PRT
<213> ORGANISM: Mycobacterium tuberculosis

<400> SEQUENCE: 13

Tyr Gln Gly Val Gln Gln Lys Trp Asp Ala Thr Ala Thr Glu Leu
1               5                   10                  15

<210> SEQ ID NO 14
<211> LENGTH: 15
<212> TYPE: PRT
<213> ORGANISM: Mycobacterium tuberculosis

<400> SEQUENCE: 14

Gln Lys Trp Asp Ala Thr Ala Thr Glu Leu Asn Asn Ala Leu Gln
1               5                   10                  15

<210> SEQ ID NO 15
<211> LENGTH: 15
<212> TYPE: PRT
<213> ORGANISM: Mycobacterium tuberculosis
```

-continued

```
<400> SEQUENCE: 15
Thr Ala Thr Glu Leu Asn Asn Ala Leu Gln Asn Leu Ala Arg Thr
1               5                   10                  15

<210> SEQ ID NO 16
<211> LENGTH: 15
<212> TYPE: PRT
<213> ORGANISM: Mycobacterium tuberculosis

<400> SEQUENCE: 16

Asn Asn Ala Leu Gln Asn Leu Ala Arg Thr Ile Ser Glu Ala Gly
1               5                   10                  15

<210> SEQ ID NO 17
<211> LENGTH: 15
<212> TYPE: PRT
<213> ORGANISM: Mycobacterium tuberculosis

<400> SEQUENCE: 17

Asn Leu Ala Arg Thr Ile Ser Glu Ala Gly Gln Ala Met Ala Ser
1               5                   10                  15

<210> SEQ ID NO 18
<211> LENGTH: 15
<212> TYPE: PRT
<213> ORGANISM: Mycobacterium tuberculosis

<400> SEQUENCE: 18

Ile Ser Glu Ala Gly Gln Ala Met Ala Ser Thr Glu Gly Asn Val
1               5                   10                  15

<210> SEQ ID NO 19
<211> LENGTH: 15
<212> TYPE: PRT
<213> ORGANISM: Mycobacterium tuberculosis

<400> SEQUENCE: 19

Gln Ala Met Ala Ser Thr Glu Gly Asn Val Thr Gly Met Phe Ala
1               5                   10                  15
```